United States Patent
Shan et al.

(12)

(10) Patent No.: US 6,297,019 B1
(45) Date of Patent: *Oct. 2, 2001

(54) RECOMBINANT POLYNUCLEOTIDES ENCODING CYP7 PROMOTER-BINDING FACTORS

(75) Inventors: Bei Shan; Masahiro Nitta, both of South San Francisco, CA (US)

(73) Assignees: Tularik Inc., South San Francisco, CA (US); Sumitomo Pharmaceuticals Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/510,654

(22) Filed: Feb. 22, 2000

Related U.S. Application Data

(62) Division of application No. 09/282,803, filed on Mar. 31, 1999, now Pat. No. 6,027,901, which is a division of application No. 09/132,619, filed on Aug. 11, 1998, now Pat. No. 5,958,697.
(60) Provisional application No. 60/067,708, filed on Dec. 8, 1997.

(51) Int. Cl.[7] .............................. C12Q 1/68; C12Q 1/02; C07H 21/04; G01N 33/53
(52) U.S. Cl. .................. 435/6; 435/7.8; 435/29; 536/23.5
(58) Field of Search .................... 536/23.5; 435/6, 435/7.8, 29, 69.1

(56) References Cited

PUBLICATIONS

Hillier et al, Genbank EST database, Accession No. R09959, Apr. 6, 1995.*

Hillier et al, Genbank EST database, Accession No. H72424, Oct. 27, 1995.*

Kudo et al. Molecular cloning of chicken FTZ–F1–related orphan receptors. Gene. Sep. 15, 1997, vol. 197, No. 1/2, pp. 261–268.

Peterson et al. Transcription factor based therapeutics: drugs of the future? Trends in Biotech. Jan. 1993, vol. 11, pp. 11–18.

Ellinger–Ziegelbauer et al., Mol. Cell. Biol., vol. 14; pp. 2786–2797. Apr., 1994.

EST Accession Nos. AA425370; AA25452; H72424; N59115; N59515.

EST Accession Nos. A56543; S27874; A46077; A56120.

* cited by examiner

Primary Examiner—Terry McKelvey
(74) Attorney, Agent, or Firm—Richard Aron Osman

(57) ABSTRACT

The invention provides methods and compositions relating to CPF proteins which regulate transcriptional activation, and related nucleic acids. The polypeptides may be produced recombinantly from transformed host cells from the disclosed CPF encoding nucleic acids or purified from human cells. The invention provides isolated CPF hybridization probes and primers capable of specifically hybridizing with the disclosed CPF genes, CPF-specific binding agents such as specific antibodies, and methods of making and using the subject compositions in diagnosis, therapy and in the biopharmaceutical industry.

20 Claims, No Drawings

RECOMBINANT POLYNUCLEOTIDES ENCODING CYP7 PROMOTER-BINDING FACTORS

This application is a divisional of U.S. application Ser. No. 09/282,803, filed Mar. 31, 1999, now U.S. Pat. No. 6,027,901, which is a divisional of U.S. application Ser. No. 09/132,619, filed Aug. 11, 1998, now U.S. Pat. No. 5,958,697, which claims priority to U.S. Provisional Application Ser. No. 60/067,708, filed Dec. 8, 1997, which are incorporated herein by reference.

INTRODUCTION

1. Field of the Invention

The field of this invention is transcription factors which bind CYP7 promoters.

2. Background

In mammalian cells, cholesterol is an essential component for membranogenesis and for the synthesis of sterols and nonsterols that are critical for normal cellular functions. Excess cholesterol, however, not only is lethal to cells but also creates a major problem in atherolsclerosis for its deposit in arteries. To maintain cholesterol homeostasis, cells, in particular liver cells, adopt three major ways to regulate cholesterol levels: 1) uptake of dietary cholesterol via LDL receptor; 2) endogenous cholesterol biosynthesis and 3) metabolic conversion of cholesterol to bile acids. The key molecule that coordinates these processes is cholesterol itself, serving as a feedback signal. When the intracellular cholesterol level increases either through cholesterol uptake or biosynthesis, the transcription of genes including LDL receptor and the key cholesterol biosynthesis enzymes such as HMG-CoA synthase and HMG-CoA reductase is repressed. These feedback processes are mediated by a novel family of transcription factors called sterol regulatory element binding proteins (SREBPs). SREBPs contain an N-terminal transcription factor domain, two hydrophobic transmembrane domains and a C-terminal regulatory domain. When the intracellular cholesterol level is low, a two-step proteolytic cascade occurs which releases the N-terminal transcription factor domain of SREBPs from the endoplasmic reticulum, moving to the nucleus where activation of the SRE-containing genes occurs.

While the SREBP pathway is responsible for regulation of genes involved in cholesterol uptake and cholesterol biosynthesis such as LDL receptor and HMG-CoA synthase, the molecular basis of cholesterol catabolism is largely unknown. The major catabolic pathway for cholesterol removal is the production of bile acids that occurs exclusively in the liver. Cholesterol 7α-hydroxylase is the first and rate-limiting enzyme in the pathway. The cholesterol 7α-hydroxylase gene, also known as CYP7, belongs to the cytochrome P-450 family that contains many microsomal enzymes involved in liver metabolism. It has been shown that the expression of the CYP7 gene is tightly regulated: it is expressed exclusively in liver; its expression can be induced by dietary cholesterol and suppressed by bile acids. It has been shown that cholesterol catabolism plays a central role in cholesterol homeostasis. Treatment of laboratory animals with cholestid or cholestyramine, two bile acid-binding resins, decreases serum cholesterol levels. Moreover, overexpression of the CYP7 gene in hamsters reduces total and LDL cholesterol levels. Thus, cholesterol 7α-hydroxylase is a potential therapeutic target for cholesterol lowering drugs and understanding the mechanisms by which expression of the CYP7 gene is regulated is of particular importance.

To study the molecular mechanisms of hepatic-specific expression of the human CYP7 gene, we used HepG2 cells as a model system since this cell line is one of the most studied hepatic cell lines and has been shown to be an appropriate cell line through studies of a number of hepatic-specific genes including the CYP7 gene. We started with DNase I hypersensitivity mapping of the human CYP7 promoter and identified a hepatic-specific element in the promoter. Consequently, we cloned the gene encoding the promoter-binding protein and identified it as a human ortholog of the nuclear orphan receptor Ftz-F1 family.

3. Relevant Art

Galarneau and Belanger (1997) unpublished, accession U93553, describe a human α1-Fetoprotein Transcription Factor (hFTF, SEQ ID NOS:7 and 8); Tugwood, J. D. Issemann, I. and Green, S. (1991) unpublished, accession M81385, describe a mouse liver receptor homologous protein (LRH-1) mRNA and conceptual translate (mLRH, SEQ ID NOS:9 and 10); and L. Galarneau et al. (1996) Mol. Cell Biol. 16, 3853–3865 disclose a partial rat gene; all having sequence similarity to the disclosed CPF polypeptides.

SUMMARY OF THE INVENTION

The invention provides methods and compositions relating to isolated CPF polypeptides, related nucleic acids, polypeptide domains thereof having CPF-specific structure and activity and modulators of CPF function, particularly CYP7 promoter binding. CPF polypeptides can regulate CYP7 promoter-linked gene activation and hence provide important regulators of cell function. The polypeptides may be produced recombinantly from transformed host cells from the subject CPF polypeptide encoding nucleic acids or purified from mammalian cells. The invention provides isolated CPF hybridization probes and primers capable of specifically hybridizing with the disclosed CPF gene, CPF-specific binding agents such as specific antibodies, and methods of making and using the subject compositions in diagnosis (e.g. genetic hybridization screens for CPF transcripts), therapy (e.g. CPF activators to activate CYP7 promoter-dependent transcription) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequence of natural cDNAs encoding human CPF polypeptides are shown as SEQ ID NOS:1, 3 and 5, and the full conceptual translates are shown as SEQ ID NOS:2, 4 and 6, respectively. The CPF polypeptides of the invention include one or more functional domains of SEQ ID NO:2, 4 or 6, which domains comprise at least 8, preferably at least 16, more preferably at least 32, most preferably at least 64 contiguous residues of SEQ ID NO:2, 4 or 6 and have human CPF-specific amino acid sequence and activity. CPF domain specific activities include CYP7 promoter-binding or transactivation activity and CPF specific immunogenicity and/or antigenicity. CPF specific polypeptide sequences distinguish hFTF and mLRH (SEQ ID NOS:8 and 10), and are readily identified by sequence comparison; see, e.g. Tables 5, 6, and 7, herein. Exemplary sequences include 10 residue domains of SEQ ID NO:2 comprising at least one of residues 1–10, 11–15, 16–21, 204–207 and 299–307, 10 residue domains of SEQ ID NO:4 comprising residue 154, and 10 residue domains of SEQ ID NO:6 comprising at least one of residues 3–10, 13–22 and 30–38.

CPF-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an CPF polypeptide with a binding target is evaluated. The binding target may be a natural intracellular binding target such as a CYP7 promoter binding site, a CPF regulating protein or other regulator that directly modulates CPF activity or its localization; or non-natural binding target such as a specific immune protein such as an antibody, a synthetic nucleic acid binding site (see consensus sequences, below), or a CPF specific agent such as those identified in screening assays such as described below. CPF-binding specificity may be assayed by binding equilibrium constants (usually at least about $10^7$ $M^{-1}$, preferably at least about $10^8$ $M^{-1}$, more preferably at least about $10^9$ $M^{-1}$), by CYP7 or synthetic binding site reporter expression, by the ability of the subject polypeptides to function as negative mutants in CPF-expressing cells, to elicit CPF specific antibody in a heterologous host (e.g a rodent or rabbit), etc. For example, in this fashion, domains defined by SEQ ID NO:2, residues 33–123 are shown to provide a functional DNA binding domain, and those defined by SEQ ID NO:2, residues 242–333 and 383–405 are shown to provide a functional ligand binding domain.

In a particular embodiment, deletion mutagenesis is used to define functional CPF domains which bind CYP7 promoter elements (see Examples, below). See, e.g. Table 1.

TABLE 1

Exemplary CPF deletion mutants defining CPF functional domains.

| Mutant | Sequence | DNA binding |
| --- | --- | --- |
| ΔN1 | SEQ ID NO: 2, residues 4–495 | + |
| ΔN2 | SEQ ID NO: 2, residues 12–494 | + |
| ΔN3 | SEQ ID NO: 2, residues 24–495 | + |
| ΔN4 | SEQ ID NO: 2, residues 33–495 | + |
| ΔN5 | SEQ ID NO: 2, residues 33–123 | + |
| ΔC1 | SEQ ID NO: 2, residues 1–408 | + |
| ΔC2 | SEQ ID NO: 2, residues 1–335 | + |
| ΔC3 | SEQ ID NO: 2, residues 1–267 | + |
| ΔC4 | SEQ ID NO: 2, residues 1–189 | + |
| ΔC5 | SEQ ID NO: 2, residues 1–124 | + |

In a particular embodiment, the subject domains provide CPF-specific antigens and/or immunogens, especially when coupled to carrier proteins. For example, peptides corresponding to CPF- and human CPF-specific domains are covalently coupled to keyhole limpet antigen (KLH) and the conjugate is emulsified in Freunds complete adjuvant. Laboratory rabbits are immunized according to conventional protocol and bled. The presence of CPF-specific antibodies is assayed by solid phase immunosorbant assays using immobilized CPF polypeptides of SEQ ID NO:2, 4 or 6, see, e.g. Table 2.

TABLE 2

Immunogenic CPF polypeptides eliciting CPF-specific rabbit polyclonal antibody: CPF polypeptide-KLH conjugates immunized per protocol described above.

| CPF Polypeptide Sequence | Immunogenicity |
| --- | --- |
| SEQ ID NO: 2, residues 1–10 | +++ |
| SEQ ID NO: 2, residues 4–15 | +++ |
| SEQ ID NO: 2, residues 8–20 | +++ |

TABLE 2-continued

Immunogenic CPF polypeptides eliciting CPF-specific rabbit polyclonal antibody: CPF polypeptide-KLH conjugates immunized per protocol described above.

| CPF Polypeptide Sequence | Immunogenicity |
| --- | --- |
| SEQ ID NO: 2, residues 12–25 | +++ |
| SEQ ID NO: 2, residues 15–30 | +++ |
| SEQ ID NO: 2, residues 19–32 | +++ |
| SEQ ID NO: 2, residues 20–29 | +++ |
| SEQ ID NO: 2, residues 200–211 | +++ |
| SEQ ID NO: 4, residues 150–159 | +++ |

The claimed CPF polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The CPF polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) or that are otherwise known in the art.

The invention provides binding agents specific to CPF polypeptides, preferably the claimed CPF polypeptides, including agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. CYP7 promoter-dependent transcriptional activation. Novel CPF-specific binding agents include CPF-specific receptors/CPF-specific binding proteins, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one, two- and three-hybrid screens, non-natural intracellular binding agents identified in screens of chemical libraries such as described below, etc. Agents of particular interest modulate CPF function, e.g. CPF-dependent transcriptional activation.

Accordingly, the invention provides methods for modulating signal transduction involving a CPF or a CYP7 promoter in a cell comprising the step of modulating CPF activity. The cell may reside in culture or in situ, i.e. within the natural host. For diagnostic uses, CPF binding agents are frequently labeled, such as with fluorescent, radioactive, chemiluminescent, or other easily detectable molecules, either conjugated directly to the binding agent or conjugated to a probe specific for the binding agent. Exemplary inhibitors include nucleic acids encoding dominant/negative mutant forms of CPF, as described above, etc.

The amino acid sequences of the disclosed CPF polypeptides are used to back-translate CPF polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural CPF-encoding nucleic acid sequences ("GCG" software, Genetics Computer Group, Inc, Madison Wis.). CPF-encoding nucleic acids used in CPF-expression vectors and incorporated into recombinant host cells, e.g. for expression and screening, transgenic animals, e.g. for functional studies such as the efficacy of candidate drugs for disease associated with CPF-modulated cell function, etc.

The invention also provides nucleic acid hybridization probes and replication/amplification primers having a CPF cDNA specific sequence comprising at least 12, preferably at least 24, more preferably at least 36 and most preferably at least contiguous 96 bases of a strand of SEQ ID NO:1, 3 or 5 sufficient to specifically hybridize with a second nucleic acid comprising the complementary strand of SEQ ID NO:1, 3 or 5 and distinguish hFTF and mLRH cDNAs (SEQ ID NOS:7 and 9). Such CPF specific sequences are readily discernable by sequence comparison; see, e.g. Table 8, herein. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 MEDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C.

TABLE 3

Exemplary CPF nucleic acids which hybridize with a strand of SEQ ID NO: 1, 3 and/or 5 under Conditions I and/or II.

| CPF Nucleic Acids | Hybridization |
| --- | --- |
| SEQ ID NO: 1, nucleotides 1–26 | + |
| SEQ ID NO: 1, nucleotides 52–62 | + |
| SEQ ID NO: 1, nucleotides 815–825 | + |
| SEQ ID NO: 1, nucleotides 1120–1135 | + |
| SEQ ID NO: 1, nucleotides 1630–1650 | + |
| SEQ ID NO: 1, nucleotides 1790–1810 | + |
| SEQ ID NO: 1, nucleotides 1855–1875 | + |
| SEQ ID NO: 1, nucleotides 1910–1925 | + |
| SEQ ID NO: 1, nucleotides 2090–2110 | + |
| SEQ ID NO: 1, nucleotides 2166–2186 | + |
| SEQ ID NO: 1, nucleotides 2266–2286 | + |
| SEQ ID NO: 1, nucleotides 2366–2386 | + |
| SEQ ID NO: 1, nucleotides 2466–2486 | + |
| SEQ ID NO: 1, nucleotides 2566–2586 | + |
| SEQ ID NO: 1, nucleotides 2666–2686 | + |
| SEQ ID NO: 1, nucleotides 2766–2786 | + |
| SEQ ID NO: 1, nucleotides 2866–2886 | + |
| SEQ ID NO: 1, nucleotides 2966–2986 | + |
| SEQ ID NO: 1, nucleotides 3066–3086 | + |

The subject nucleic acids are of synthetic/non-natural sequences and/or are isolated, i.e. unaccompanied by at least some of the material with which they are associated in their natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than those which they are joined to on a natural chromosome. Recombinant nucleic acids comprising the nucleotide sequence of SEQ ID NO:1, 3 or 5, or requisite fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of CPF genes and gene transcripts and in detecting or amplifying nucleic acids encoding additional CPF homologs and structural analogs. In diagnosis, CPF hybridization probes find use in identifying wild-type and mutant CPF alleles in clinical and laboratory samples. Mutant alleles are used to generate allele-specific oligonucleotide (ASO) probes for high-throughput clinical diagnoses. In therapy, therapeutic CPF nucleic acids are used to modulate cellular expression or intracellular concentration or availability of active CPF.

The invention provides efficient methods of identifying agents, compounds or lead compounds for agents active at the level of a CPF modulatable cellular function. Generally, these screening methods involve assaying for compounds which modulate CPF interaction with a natural CPF binding target. A wide variety of assays for binding agents are provided including labeled in vitro protein-protein binding assays, immunoassays, DNA-binding assay, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including a CPF polypeptide, which may be part of a fusion product with another peptide or polypeptide, e.g. a tag for detection or anchoring, etc. The assay mixtures comprise a natural intracellular CPF binding target. While native full-length binding targets may be used, it is frequently preferred to use portions (e.g. oligonucleotides) thereof so long as the portion provides binding affinity and avidity to the subject CPF polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents. etc. may be used.

The resultant mixture is incubated under conditions whereby, but for the presence of the candidate pharmacological agent, the CPF polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the CPF polypeptide and one or more binding targets is detected by any convenient way. A difference in the binding affinity of the CPF polypeptide to the target in the absence of the agent as compared with the binding affinity in the presence of the agent indicates that the agent modulates the binding of the CPF polypeptide to the CPF binding target. Analogously, in the cell-based assay also described below, a difference in CPF-dependent transcriptional activation in the presence and absence of an agent indicates the agent modulates CPF function. A difference, as used herein, is statistically significant and preferably represents at least a 50%, more preferably at least a 90% difference.

The following experimental section and examples are offered by way of illustration and not by way of limitation.

EXAMPLES

1. Isolation and Characterization of CPF and CYP7 Promoter Elements

Cells and Plasmids HepG2, a human hepatoma cell line, 293, a transformed embryonic kidney cell line, and Caco2, a colon adenocarcinoma cell line are purchased from ATCC. SV589 is a transformed human fibrablast line. Cells were cultured in Dulbecco's modified Eagle's medium-Ham's F12 (1:1) supplemented with 10% fetal calf serum at 37° C., 5%CO in a humidified incubator. pGL3:CYP7 contains a DNA fragment of −716/+14 region of the human CYP7α gene, which was cloned into the pGL3-luciferase reporter plasmid (Promega). pGL3:SFM or pGL3:BAM contains mutations at the positions of −130 and −129 (GG to TT) or of −62 and −61 (AA to TC) respectively. The two base pair substitutions were introduced into pGL3:CYP7 by using ExSite mutagenesis kit (Stratagene). pGL3:3×wt and pGL3:3×mut were constructed by cloning three tendon repeats of either wild type of −135 to −118 of the promoter or the repeats with two base pair substitutions of G to T at the positions of −130 and −129 into a modified pGL3 with an TATA sequence from the HSV TK gene. pfCPF contains a flag tagged sequence at the N terminus of the gene which was cloned into pCDNA3 (Invitrogene). pfCPF-AF2 has an 15 amino acid deletion of the AF-2 domain at the C terminus of the gene. pfCPF-VP contains a transactivation domain (aa412–490) of HSV VP16 which replaces the AF-2 domain of pfCPF.

Dnase I hypersensitivity mapping Cells (3×10$^6$) were harvested and lysed in 1.5 ml of lysis buffer containing 50 mM Tris-HCl pH 7.9, 100 mM KCl, 5 mM MgCl$_2$, 0.05% saponin, 200 mM 2-mercaptoethanol, 50% glycerol. Nuclei were collected by centrifugation and resuspended in the buffer containing 100 mM NaCl, 50 mM Tris-HCl pH 7.9, 3 mM MgCl$_2$, 1 mM DTT, 1×complete protease inhibitor cocktail (Boeringer Mannheim), and sequentially diluted DNase I (5, 1.7, 0.6 units/ml). Nuclei suspensions were incubated at 37° C. for 20 min. The reactions were stopped by adding EDTA to a final concentration of 100 mM. After RNase A and Protease K treatment, genomic DNA was prepared and subjected to southern hybridization.

Electrophoretic mobility shift assay Nuclear extracts were prepared from cultured cells using KCl instead of NaCl. In vitro transcription and translation were performed with a TNT system (Promega). 1 μg of protein of nuclear extracts or 0.1~1 μl of in vitro translated product was mixed with 40,000 cpm of $^{32}$P labeled oligonucleotide in the reaction buffer containing 10 mM Hepes (pH7.6), 1 μg of poly (dI-dC), 100 mM KCl, 7% glycerol, 1 mM EDTA, 1 mM DTT, 5 mM MgCl$_2$, and 40 pmoles unrelated single strand oligo DNA, and incubated for 20 min at room temperature. Reaction mixtures were separated on 4% polyacrylamide-0.5×TBE gel. Gels were dried and exposed to X-ray films.

In competition experiments, 30 or 60 fold molar excess of competitor DNA was added. In antibody supershift experiments, an anti-CPF antiserum or pre-immune serum was added to the reaction mixtures prior to the addition of probe DNA.

Transfection and reporter gene analysis One day before transfection, cells were plated on 6-well dishes (4×10$^5$/well). In general, 2 ug of luciferase reporter plasmid along with 0.1 ug of RSV LTR driven b-galactosidase expression vector was transfected by the calcium phosphate method into cultured cells for 48 hours. Cell extracts were prepared and assayed for the luciferase activity using Luciferase assay system (Promega). Luciferase activity was normalized by the b-galactosidase activity.

Molecular cloning of CPF. A human EST clone (GenBank accession number N59515) which contains the Ftz-F1 box sequence was used to screen a human liver cDNA library purchased from Clontech. cDNAs in positive clones were recovered by conversion of phage DNA into pTriplEx plasmids and sequenced. Among several positive clones which might be alternative spliced forms from the same gene, one clone (pTriplEx-113) was selected for further analysis.

Tissue-specific expression of CPF. Northern blots of polyA+RNA from human tissues were purchased from Clontech. Hybridization reaction was carried out with the Northern MAX hybridization buffer (Ambion).

Immunoprecipitation. Peptide derived from CPF cDNA sequence (DRMRGGRNFKGPMYKRDR) (SEQ ID NO 6, residues 159–176) was used to raise an anti-CPF polyclonal antibody. HepG2 or 293 cells (1×10$^7$) were cultured in the media containing 100 μCi/ml of $^{35}$S-methionine for 30 min. Cells were harvested and lysed by 3 times of freeze-thaw in the buffer containing 50 mM Tris-HCl pH7.5, 125mM NaCl, 5 mM EDTA, 0.1% NP-40. Cell lysates were then used for immunoprecipitation with the anti-CPF antibody. Precipitated samples were separated by 10% SDS-PAGE and exposed to X-ray films.

Dnase I hypersensitive site mapping of the human CYP7 gene. To study the mechanisms of hepatic-specific expression of the human CYP7 gene, we first attempted to identify the putative elements responsible for the hepatic-specific expression by DNase I hypersensitivity mapping of the gene. DNase I hypersensitivity is known to be associated with the activity of transcription. Nuclei prepared from HepG2, 293 and Caco2 cells were treated with the increasing amount of DNase I. DNA was then extracted, digested with the proper restriction enzymes, and probed by Southern blotting with a labeled fragment containing nucleotide from −944 to −468. In addition to a predicted 5 kb Pst I fragment, a second 2.8 kb band was observed. The increased intensity of the 2.8 kb band, accompanied by the decreased intensity of the parental 5 kb band in parallel with the increased amount of DNase I treatment, indicated the existence of a DNase I hypersensitive site. Importantly, the 2.8 kb band was only shown in HepG2 cells but not in other cells examined. The size of the fragment indicates that the hepatic-specific DNase I hypersensitive site is localized between −100 bp to −300 bp relative to the transcriptional initiation site of the human CYP7 gene. The location of the site was further confirmed by using different restriction enzymes with probes from different regions.

Identification of a hepatic-specific CYP7 promoter element. To further identify the hepatic-specific element of the CYP7 gene, seven overlapped oligonucleotides (CL5, bp −368-291; CL6, bp −311-232; CL7, bp −256-177; CL1, bp −201-122; CL2, bp −140-61; CL 3, bp −121-42; CL4, bp −60-+20) were synthesized and used in gel mobility shift experiment There were hepatocytic-specific DNA-protein complexes formed when labeled oligonucleotide CL1 and oligonucleotide CL2 were used. The oligonucleotides CL1 and CL2 apparently recognized the same complex since unlabeled oligonucleotide CL1 competed with oligonucleotide CL2. This DNA-protein complex is sequence specific since they can be competed by excess of unlabeled oligonucleotides CL1 and CL2, but not by oligonucleotides next to this region, CL3–7. This promoter complex was observed only with HepG2 nuclear extracts but not with 293, Caco2 or SV589 nuclear extracts, consistent with the hepatic-specific DNase I hypersensitive site identified above. The sequence overlapped with these two oligonucleotides is apparently responsible for the hepatic-specific DNA-protein complex.

Sequence analysis revealed that this region contains several six bp repeated elements, known to be the binding sites for nuclear hormone receptors. To determine the exact sequences responsible for the hepatic-specific binding, several oligonucleotides that contain mutations in each of the repeats or adjacent sequences were synthesized. As shown in Table 5, while oligonucleotides containing mutations in repeats A and B competed complex formation, oligonucleotides containing mutations in repeat C failed to compete, indicating that repeat C is essential for the binding. To further determine the nucleotides required for complex formation, a number of oligonucleotides containing detailed mutations in repeat C and adjacent sequences were synthesized and used in gel shift experiments. Our results indicated that a consensus element containing nine nucleotides is required for the complex formation. This element is known to be a binding site for a family of nuclear hormone receptor called Ftz-F1.

TABLE 4

| Oligonucleotide | DNA Binding |
| --- | --- |
| TCTGATACCTGTGGACTTAGTTCAAGGCCAGTTA(SEQ ID NO: 11) | + |
| TCTGGAGGATGTGGACTTAGTTCAAGGCCAGTTA(SEQ ID NO: 12) | + |
| TCTGATACCTGTTATATTAGTTCAAGGCCAGTTA(SEQ ID NO: 13) | + |
| TCTGGAGGATGTGGACTTCTATCAAGGCCAGTTA(SEQ ID NO: 14) | + |
| TCTGATACCTGTTATATTCTATCAAGGCCAGTTA(SEQ ID NO: 15) | + |
| TCTGGAGGATGTGGACTTAGTTCACACAGAGTTA(SEQ ID NO: 16) | + |
| TCTGATACCTGTGGACTTAGTAGAAGGCCAGTTA(SEQ ID NO: 17) | − |
| TCTGATACCTGTGGACTTAGTTCTTGGCCAGTTA(SEQ ID NO: 18) | − |
| TCTGATACCTGTGGACTTAGTTCAATGCCAGTTA(SEQ ID NO: 19) | − |
| TCTGATACCTGTGGACTTAGTTCAAGTCCAGTTA(SEQ ID NO: 20) | − |
| TCTGATACCTGTGGACTTAGTTCAAGGAGAGTTA(SEQ ID NO: 21) | − |
| TCTGATACCTGTGGACTTAGTTCAAGGCCTATTA(SEQ ID NO: 22) | − |
| TCTGATACCTGTGGACTTAGTTCAAGGCCAATTA(SEQ ID NO: 23) | + |
| TCTGATACCTGTGGACTTAGTTCAAGGCCAGGTA(SEQ ID NO: 24) | + |
| TCAAGGCCA | CYP7P-Binding Site |
| YCAAGGYCR | FTZ-F1 consensus |
| AAAGGTCA | NGFI-B consensus |
| TCTGATACCTGTGGACTTAGTCAAAGGCCAGTTA(SEQ ID NO: 25) | − |
| TCTGATACCTGTGGACTTAGTACCAGGCCAGTTA(SEQ ID NO: 26) | − |
| TCTGATACCTGTGGACTTAGTAGGAGGCCAGTTA(SEQ ID NO: 27) | − |
| TCTGATACCTGTGGACTTAGTAAGAGGCCAGTTA(SEQ ID NO: 28) | − |
| TCTGATACCTGTGGACTTAGTTTCAGGCCAGTTA(SEQ ID NO: 29) | − |
| TCTGATACCTGTGGACTTAGTCTCAGGCCAGTTA(SEQ ID NO: 30) | − |

Ftz-F1 binding site is essential for the hepatic-specific expression of the human CYP7 gene. To determine the role of the Ftz-F1 site in human CYP7 gene expression, the site was mutated by 2 nucleotide substitutions. As a control, mutations at an unrelated region were also created. The promoter sequence of +14 to −716 containing either the wild type or mutated Ftz-F1 site, or control was cloned into a luciferase reporter plasmid pGL3. The plasmid DNA was then transfected into HepG2, 293 and Caco2 cells and promoter activity was measured by luciferase activity. Mutations in the Ftz-F1 site completely abolished promoter activity in HepG2 cells while showing little or no effects on 293 and Caco2 cells. As a control, mutations in the unrelated region showed no effect on promoter activity in all cells examined.

Cloning of the hepatic-specific CYP7 promoter-binding protein. Nuclear hormone receptors are DNA-specific, often ligand-dependent, transcription factors. Ftz-F1, a drosophila DNA-binding protein, is the prototype of a subgroup of the nuclear hormone receptor family. Like most of the nuclear hormone receptors, Ftz-F1 contains a zinc finger DNA-binding domain and a putative ligand-binding domain. The DNA-binding domain of the Ftz-F1 family members contains a unique 26 amino acid extension (called Ftz-F1 box) at C terminus of the two zinc finger modules. The sequence of Ftz-F1 box is conserved from drosophila to rodent, and is largely responsible for the sequence-specific binding to DNA. The identification of the Ftz-F1 binding site in the human CYP7 promoter suggests that a human Ftz-F1-like protein binds to the Ftz-F1 element in the human CYP7 gene. To clone the human version of Ftz-F1, a DNA sequence of the Ftz-F1 box was used to search an EST database and a human EST clone was found. This EST sequence was then used as the probe to screen a human liver cDNA library. Several clones were isolated and one of them, clone #113, was used for further analysis.

Characterization of CPF. Clone #113 encodes a full length polypeptyde of 495 amino acids, with an in-frame stop codon 30 nucleotides upstream of the first ATG. We named the protein as CPF for CYP7 Promoter-binding Factor. Sequence analysis reveals that CPF is a new member of the Ftz-F1 family. The closest homologs of CPF are the mouse version of the family, LRH-1 (SEQ ID NOS:7, 8)and a human variant, hFTF (SEQ ID NOS:9, 10). To confirm the cloned CPF is the factor responsible for the CYP7 promoter binding activity, in vitro translated CPF was used side-by-side with the HepG2 nuclear extracts in gel shift experiments. We found in vitro translated CPF recognized the same DNA sequence as the endogenous protein does and the gel shift patterns between these two appear to be identical. Antibodies raised against a peptide containing the Ftz-F1 box were used in gel shift experiments. We found the DNA-protein complex formed either with HepG2 nuclear extracts or with in vitro translated CPF was disrupted by the specific antibody but not by preimmune serum. Furthermore, the antibody recognized a hepatic-specific cellular protein that comigrates with the in vitro translated CPF. The endogenous gene product recognized by the Ftz-F1-specific antibody is apparently hepatic specific since there is no corresponding protein in 293 cells.

Transcriptional activity of CPF. To determine the transcriptional activity of CPF, flag tagged expression plasmid pfCPF was used to be transfected into 293 cells with luciferase reporter plasmids containing three copies of wild type Ftz-F1 binding site. We found pfCPF has a limited transcriptional activity. To determine whether the weak transcriptional activity is due to the weak transcription domain AF2 of the gene whose activity is probably also ligand dependent, pfCPF-VP was constructed by replacing the AF2 domain of CPF with a strong viral transactivation domain. When fCPF-VP was tranfected into 293 cells together with the reporter plasmid, a strong transcriptional activity was observed, suggesting that transcriptional activation of CPF requires help from either a ligand-dependent process or a cofactor.

Tissue specific expression of CPF. It has been reported that in rodents CYP7 gene is exclusively expressed in liver. To determine the tissue specific expression of the CPF gene, a pair of RNA tissue blots were probed either with labeled CPF cDNA or with CYP7 cDNA. We found the expression of the CPF gene apparently enriched in pancreas and liver, with a low level of expression in heart and lung, and little or no expression in other tissues. The human CYP7 is apparently expressed only in liver. Interestingly, a pancreas-specific transcript with a lower molecular weight was recognized by the human CYP7 probe.

2. High-Throughput In Vitro Fluorescence Polarization Assay Reagents

Sensor: Rhodamine-labeled ILRKLLQE SEQ ID NO:11 peptide (final conc.=1–5 nM)

Receptor: Glutathione-S-transferase/CPF ligand binding domain (SEQ ID NO:2. residues 1–123) fusion protein (final conc.=100–200 nM)

Buffer: 10 mM HEPES, 10 mM NaCl, 6 mM magnesium chloride, pH 7.6

Protocol:

1. Add 90 microliters of Sensor/Receptor mixture to each well of a 96-well microtiter plate.
2. Add 10 microliters of test compound per well.
3. Shake 5 min and within 5 minutes determine amount of fluorescence polarization by using a Fluorolite FPM-2 Fluorescence Polarization Microtiter System (Dynatech Laboratories, Inc).

3. Protocol for Cell-Based Reporter Assay

CPF can trans-activate FTZ-F1 reporter constructs when overexpressed in 293 cells or HeLa cells. 293 cells are transfected using the calcium phosphate precipitation method with a plasmid encoding a 3 FTZ-F1 binding site-luciferase reporter construct and various amounts of expression vector encoding CPF. After 36–48 hours, cells are left untreated or treated with candidate ligand (10–50 ng/ml) for 6 hours prior to harvest. Cells are lysed and luciferase activity measured using the luciferase assay kit (Promega). The luciferase activity in each transfection is normalized by co-transfecting a pRSV-β gal control vector.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 5

```
113PRO = SEQ ID NO:2
hFTFpro = SEQ ID NO:8

113PRO    MSSNSDTGDL QESLKHG---  -LTP--IVSQ FKMVNYSYDE DLEELCPVCG  44
hFTFpro   MLPKVETEAL GLARSHGEQG QMPENMQVSQ FKMVNYSYDE DLEELCPVCG  50

113PRO    DKVSGYHYGL LTCESCKGFF KRTVQNNKRY TCXENQNCQI DKTQRKRCPY  94
hFTFpro   DKVSGYHYGL LTCESCKGFF KRTVQNNKRY TCXENQNCQX DKTQRKRCPY 100
```

TABLE 5-continued

```
113PRO = SEQ ID NO:2
hFTFpro = SEQ ID NO:8
```

| | | | | | |
|---|---|---|---|---|---|
| 113PRO | CRFQKCLSVG | MKLEAVRADR | MRGGRNKFGP | MYKRDRALKQ | QKKALIRANG 144 |
| hFTFpro | CRFQKCLSVG | MKLEAVRADR | MRGGRNKFGP | NYKRDRALKQ | QKKALIRANG 150 |
| | | | | | |
| 113PRO | LKLEAMSQVI | QAMPSDLTXS | SAIQNIHSAS | KGLPLNHAAL | PPTDYDRSPF 194 |
| hFTFpro | LKLEAMSQVI | QAMPSDLTXS | SAIQNXHSAS | KGLPLNHAAL | PPTDYDRSPF 200 |
| | | | | | |
| 113PRO | VTSPISMTMP | PHGSLQGYQT | YGHFPSRAIK | SEYPDPYTSS | PESIMGYSYM 244 |
| hFTFpro | VTSPXSMTM- | LHGSLQGYQT | YGHFPSRAXK | SEYPDPYTSS | PESXMGYSYM 249 |
| | | | | | |
| 113PRO | DSYQTSSPAS | IPHLILELLK | CEPDEPQVQA | KIMAYLQQEQ | ANRSKHEKLS 294 |
| hFTFpro | DSYQTSSPAS | XPHLILELLK | CEPDEPQVQA | KXMAYLQQEQ | ANRSKHEKLS 299 |
| | | | | | |
| 113PRO | TFGLMCKMAD | QTLFSXVEWA | RSSIFFRELK | VDDQMKLLQN | CWSELLXLDH 344 |
| hFTFpro | TFGLMCKMAD | QTVFSXVEWA | RSSXFFRELK | VDDQMKLLQN | CWSELLXLDH 349 |
| | | | | | |
| 113PRO | IYRQVVHGKE | GSIFLVTGQQ | VDYSXXASQA | GATLNNLMSH | AQELVAKLRS 394 |
| hFTFpro | IYRQVVHGKE | GSXFLVTGQQ | VDYSXXASQA | GATLNNLMSH | AQELVAKLRS 399 |
| | | | | | |
| 113PRO | LQFDQREFVC | LKFLVLFSLD | VKNLENFQLV | EGVQEQVNAA | LLDYTMCNYP 444 |
| hFTFpro | LQFDQREFVC | LKFLVLFSLD | VKNLENFQLV | EGVQEQVNAA | LLDYTMCNYP 449 |
| | | | | | |
| 113PRO | QQTEKFGQLL | LRLPEIRAXS | MQAEEYLYYK | HLNGDVPYNN | LLIEMLHAKR 494 |
| hFTFpro | QQTEKFGQLL | LRLPEIRAXS | MQAEEYLYYK | HLNGDVPYNN | LLXEMLHAKR 499 |
| | | | | | |
| 113PRO | A | | | | 495 |
| hFTFpro | A | | | | 500 |

TABLE 6

```
113PRO = SEQ ID NO:2
36PR0 = SEQ ID NO:4
hFTFpro = SEQ ID NO:8
mLRHpro = SEQ ID NO:10
```

| | | | | | |
|---|---|---|---|---|---|
| 113PRO | MSSNSDTGDL | QESLKHG--- | ---------- | ---------- | ---------- 17 |
| 36pro | MSSNSDTGDL | QESLKHG--- | ---------- | ---------- | ---------- 17 |
| hFTFpro | MLPKVETEAL | GLARSHG--- | ---------- | ---------- | ---------- 17 |
| mLRHpro | MSASLDTGDF | QEFLKHGLTA | IASAPGSETR | HSPKREEQLR | EKRAGLPDRH 50 |
| | | | | | |
| 113PRO | ---------- | ---------- | ---------- | --LTP--IVS | QFKNVNYSYD 33 |
| 36pro | ---------- | ---------- | ---------- | --LTP--IVS | QFKMVNYSYD 33 |
| hFTFpro | ---------- | ---------- | --------EQ | GQMPENMQVS | QFKMVNYSYD 39 |
| mLRHPRO | RRPIPARSRL | VMLPKVETEA | PGLVRSHGEQ | GQMPENMQVS | QFKMUNYSYD 100 |
| | | | | | |
| 113PRO | EDLEELCPVC | GDKVSGYHYG | LLTCESCKGF | FKRTVQNNKR | YTCIENQNCQ 83 |
| 36pro | EDLEELCPVC | GDKVSGYHYG | LLTCESCKGF | FKRTVQNNKR | YTCIENQNCQ 83 |
| hFTFpro | EDLEELCPVC | GDKVSGYHYG | LLTCESCKGF | FKRTVQNNKR | YTCIENQNCQ 89 |
| mLRHpro | EDLEELCPVC | GDKVSGYHYG | LLTCESCKGF | FKRTVQNQKR | YTCIENQNCQ 150 |
| | | | | | |
| 113PRO | IDKTQRKRCP | YCRFQKCLSV | GNKLEAVRAD | RMRGGRNKFG | PNYKRDRALK 133 |
| 36pro | IDKTQRKRCP | YCRFQKCLSV | GNKLEAVRAD | RMRGGRNKFG | PMYRRDRALK 133 |
| hFTFpro | IDKTQRKRCP | YCRFQKCLSV | GNKLEAVRAD | RMRGGRNKFG | PNYKRDRALK 139 |
| mLRHpro | IDKTQRKRCP | YCRFKKCIDV | GMKLEAVRAD | RMRGGRNKFG | PNYKRDRALK 200 |
| | | | | | |
| 113PRO | QQKKALIRAN | GLKLEAMSQV | IQAMPSDLTI | SSAIQNIHSA | SKGLPLNHAA 183 |
| 36pro | QQKKALIRAN | GLKLEAMSQV | D--------- | ---------- | ---------- 154 |
| hFTFpro | QQKKALIRAN | GLKLEAMSQV | IQAMPSDLTI | SSAIQNIHSA | SKGLPLNHAA 189 |
| mLRHpro | QQKKALIRAN | GLKLEAMSQV | IQAMPSDLT- | -SAIQNIHSA | SKGLPLSHVA 248 |
| | | | | | |
| 113PRO | LPPTDYDRSP | FVTSPISMTM | PPHGSLQGYQ | TYGHFPSRAI | KSEYPDPYTS 233 |
| 36pro | ---------- | ---------- | ---------- | ---------- | ---------- 154 |
| hFTFpro | LPPTDYDRSP | FVTSPISMTM | -LHGSLQGYQ | TYGHFPSRAI | KSEYPDPYTS 238 |
| mLRHpro | LPPTDYDRSP | FVTSPISMTM | PPHSSLHGYQ | PYGHFPSRAI | KSEYPDPYSS 298 |
| | | | | | |
| 113PRO | SPESIMGYSY | MDSYQTSSPA | SIPHLILELL | KCEPDEPQVQ | AKIMAYLQQE 283 |
| 36pro | ---------- | ---------- | ---------- | ---------- | ---------- 154 |
| hFTFpro | SPESIMGYSY | MDSYQTSSPA | SIPHLILELL | KCEPDEPQVQ | AKIMAYLQQE 288 |
| mLRHpro | SPESMMGYSY | MDGYQTNSPA | SIPHLILELL | KCEPDEPQVQ | AKIMAYLQQE 348 |
| | | | | | |
| 113PRO | QANRSKHEKL | STFGLMCKMA | DQTLFSIVEW | ARSSIFFREL | KVDDQMKLLQ 333 |
| 36pro | ---------- | ---------- | ---------- | ---------- | ---DQMKLLQ 161 |
| hFTFpro | QANRSKHEKL | STFGLMCKMA | DQTVFSIVEW | ARSSIFFREL | KVDDQMKLLQ 338 |
| mLRHpro | QSNRNRQEKL | SAFGLLCKMA | DQTLFSIVEW | ARSSIFFREL | KVDDQMKLLQ 398 |

TABLE 6-continued

```
113PRO = SEQ ID NO:2
36PR0  = SEQ ID NO:4
hFTFpro = SEQ ID NO:8
mLRHpro = SEQ ID NO:10
```

```
113PRO   NCWSELLILD HIYRQVVHGK EGSIFLVTGQ QVDYSIIASQ AGATLNNLMS  383
36pro    NCWSELLILD HIYRQVVHGK EGSIFLVTGQ QVDYSIIASQ AGATLNNLMS  211
hFTFpro  NCWSELLILD HIYRQVVHGK EGSIFLVTGQ QVDYSIIASQ AGATLNNLMS  388
mLRHpro  NCWSELLILD HIYRQVAHGK EGTIFLVTGE HVDYSTIISH TEVAFNNLLS  448

113PRO   HAQELVAKLR SLQFDQREFV CLKFLVLFSL DVKNLENFQL VEGVQEQVNL  433
36pro    HAQELVAKLR SLQFDQREFV CLKFLVLFSL DVKNLENFQL VEGVQEQVNA  261
hFTFpro  HAQELVAKLR SLQFDQREFV CLKFLVLFSL DNKNLENFQL VEGVQEQVNA  438
mLRHpro  LAQELVVRLR SLQFDQREFV CLKFLVLFSS DNKNLENLQL VEGVQEQVNA  498

113PRO   ALLDYTMCNY PQQTEKFGQL LLRLPEIRAI SMQAEEYLYY KHLNGDVPYN  483
36pro    ALLDYTMCNY PQQTEKFRQL LLRLPEIRAI SMQAEEYLYY KHLNGDVPYN  311
hFTFpro  ALLDYTMCNY PQQTEKFGQL LLRLPEIRAI SMQAEEYLYY KHLNGDVPYN  488
mLRHpro  ALLDYTVCNY PQQTEKFGQL LLRLPEXRAI SKQAEDYLYY KHVNGDVPYN  548

113PRO   NLLIENLHAK RA                                            495
36pro    NLLIENLHAK RA                                            323
hFTFpro  NLLIEMLHAK RA                                            500
mLRHpro  NLLIEMLHAK RA                                            560
```

TABLE 7

```
105pro  = SEQ ID NO:6
hFTFpro = SEQ ID NO:8
mLRHpro = SEQ ID NO:10
```

```
105pro   MSSNSDTGDL QESLKHGLTP IG-------- ---------- ---AGLPDRH   29
hFTFpro  ---------- ---------- ---------- ---------- ----------
mLRHpro  MSASLDTGDF QEFLKHGLTA IASAPGSETR HSPKREEQLR EKRAGLPDRH   50

105pro   GSPIPARGRL VMLPKVETEA LGLARSHGEQ GQMPENMQVS QFKHTNYSYD   79
hFTFpro  ---------- -MLPKVETEA LGLARSHGEQ GQMPENMQVS QFKNVNYSYD   39
mLRHpro  RRPIPARSRL VNLPKVETEA PGLVRSHGEQ GQMPENMQVS QFKNUNYSYD  100

105pro   EDLEELCPVC GDKVSGYHYG LLTCESCKGF FKRTVQNNKR YTCIENQNCQ  129
hFTFpro  EDLEELCPVC GDKVSGYHYG LLTCESCKGF FKRTVQNNKR YTCXENQNCQ   89
mLRHpro  EDLEELCPVC GDKVSGYHYG LLTCESCKGF FKRTVQNQKR YTCIENQNCQ  150

105pro   IDKTQRKRCP YCRFQKCLSV GMKLEAVRAD RNRGGRKKFG PMYKRDRALK  179
hFTFpro  IDKTQRKRCP YCRFQKCLSV GMKLEAVRAD RMRGGRNKFG PMYKRDRALK  139
mLRHpro  IDKTQRKRCP YCRFKKCIDV GMKLEAVRAD RMRGGRNKFG PMYKRDRALK  200

105pro   QQKKALIRAN GLKLEAMSQV IQAMPSDLTI SSAXQNXHSA SKGLPLNHAA  229
hFTFpro  QQKKALXRAN GLKLEAMSQV IQAMPSDLTI SSAXQNIHSA SKGLPLNHAA  189
mLRHpro  QQKKALXRAN GLKLEAMSQV IQAMPSDLT- -SAXQNXHSA SKGLPLSHVA  248

105pro   LPPTDYDRSP FVTSPXSMTM PPHGSLQGYQ TYGHFPSRAI KSEYPDPYTS  279
hFTFpro  LPPTDYDRSP FVTSPXSMTM -LHGSLQGYQ TYGHFPSRAI KSEYPDPYTS  238
mLRHpro  LPPTDYDRSP FVTSPXSMTM PPHSSLHGYQ PYGHFPSRAI KSEYPDPYSS  298

105pro   SPESIMGYSY MDSYQTSSPA SXPHLILELL KCEPDEPQVQ AKXMAYLQQE  329
hFTFpro  SPESIMGYSY MDSYQTSSPA SXPHLXLELL KCEPDEPQVQ AKXMAYLQQE  288
mLRHpro  SPESMMGYSY MDGYQTNSPA SXPHLXLELL KCEPDEPQVQ AKXMAThQQE  348

105pro   QANRSKHEKL STFGLMCKMA DQTLFSXVEW ARSSXFFREL KVDDQMKLLQ  379
hFTFpro  QANRSKHEKL STFGLMCKMA DQTVFSXVEW ARSSXFFREL KVDDQMKLLQ  338
mLRHpro  QSNRNRQEKL SAFGLLCKMA DQTLFSXVEW ARSSXFFREL KVDDQMKLLQ  398

105pro   NCWSELLILD HIYRQVVHGK EGSIFLVTGQ QVDYSIIASQ AGATLNNLMS  429
hFTFpro  NCWSELLILD HIYRQVVHGK EGSIFLVTGQ QVDYSIIASQ AGATLNNLMS  388
mLRHpro  NCWSELLILD HIYRQVAHGK EGTIFLVTGE HVDYSTIISH TEVAFNNLLS  448

105pro   HAQELVAKLR SLQFDQREFV CLKFLVLFSL DNKNLENFQL VEGVQEQVNA  479
hFTFpro  HAQELVAKLR SLQFDQREFV CLKFLVLFSL DNKNLENFQL VEGVQEQVNA  438
mLRHpro  LAQELVVRLR SLQFDQREFV CLKFLVLFSS DVKNLENLQL VEQVQEQVNA  498

105pro   ALLDYTMCNY PQQTEKFGQL LLRLPEIRAI SMQAEEYLYY KHLNGDVPYN  529
hFTFpro  ALLDYTMCNY PQQTEKFGQL LLRLPEIRAI SHQAEEYLYY KHLNGDVPYN  488
mLRHpro  ALLDYTVCNY PQQTEKFQQL LLRLPEZRAX SKQAEDYLYY KHVNGDVPYN  548
```

TABLE 7-continued

```
105pro = SEQ ID NO:6
hFTFpro = SEQ ID NO:8
mLRHpro = SEQ ID NO:10
```

```
105pro    NLLIENLHAK RA                                541
hFTFpro   NLLIEMLHAK RA                                500
mLRHpro   NLLIEMLHAK RA                                560
```

TABLE 8

```
113 = SEQ ID NO:1
hFTF = SEQ ID NO:7
```

```
113  ---------- ---------- ---------- --------GA AAAAAGTACA  12
hFTF GAAACTGGAT ACATGGTTTA CAGCAGGTCA CTAATGTTGG AAAAAGTACA  50

113  GAGTCCAGGG AAAAGACTTG CTTGTAACTT TATGAATTCT GGATTTTTTT  62
hFTF GAGTCCAGGG AAA-GACTTG CTTGTAACTT TATGAATTCT GGL---TTTT  96

113  TTTTCCTTTG CTTTTTCTTA ACTTTCACTA AGGGTTACTG TAGTCTGATG  112
hFTF TTTTCCTTTG CTTTTTCTTA ACTTTCACTA AGGGTTACTG TAGTCTGATG  146

113  TGTCCTTCCC AAGGCCACGA AATTTGACAA GCTGCACTTT TCTTTTGCTC  162
hFTF TGTCCTTCCC AAGGCCACGA AATTTGACAA GCTGCACTTT TCTTTTGCTC  196

113  AATGATTTCT GCTTTAAGCC AAAGAACTGC CTATAATTTC ACTAAGAATG  212
hFTF AATGATTTCT GCTTTAAGCC AAAGAACTGC CTATAATTTC ACTAAGAATG  246

113  TCTTCTAATT CAGATACTGG GGATTTACAA GAGTCTTTAA AGCACGGACT  262
hFTF TCTTCTAATT CAGATACTGG GGATTTACAA GAGTCTTTAA AGCACGGACT  296

113  TACACCTATT ---------- ---------- ---------- ----------  272
hFTF TACACCTATT GGTGCTGGGC TTCCGGACCG ACACGGATCC CCCATCCCGC  346

113  ---------- ---------- ---------- ---------- ----------  272
hFTF CCGCGGTCGC CTTGTCATGC TGCCCAAAGT GGAGACGGAA GCCCTGGGAC  396

113  ---------- ---------- ---------- ---------- -------GTG  275
hFTF TGGCTCGATC GCATGGGAA CAGGGCCAGA TGCCGGAAAA CATGCAAGTG  446

113  TCTCAATTTA AAATGGTGAA TTACTCCTAT GATGAAGATC TGGAAGAGCT  325
hFTF TCTCAATTTA AAATGGTGAA TTACTCCTAT GATGAAGATC TGGAAGAGCT  496

113  TTGTCCCGTG TGTGGAGATA AGTGTCTGG GTACCATTAT GGGCTCCTCA  375
hFTF TTGTCCCGTG TGTGGAGATA AGTGTCTGG GTACCATTAT GGGCTCCTCA  546

113  CCTGTGAAAG CTGCAAGGGA TTTTTTAAGC GAACAGTCCA AAATAATAAA  425
hFTF CCTGTGAAAG CTGCAAGGGA TTTTTTAAGC GAACAGTCCA AAATAATAAA  596

113  AGGTACACAT GTATAGAAAA CCAGAACTGC CAAATTGACA AAACACAGAG  475
hFTF AGGTACACAT GTATAGAAAA CCAGAACTGC CAAATTGACA AAACACAGAG  646

113  AAAGCGTTGT CCTTACTGTC GTTTTCAAAA ATGTCTAAGT GTTGGAATGA  525
hFTF AAAGCGTTGT CCTTACTGTC GTTTTCAAAA ATGTCTAAGT GTTGGAATGA  696

113  AGCTAGAAGC TGTAAGGGCC GACCGAATGC GTGGAGGAAG GAATAAGTTT  575
hFTF AGCTAGAAGC TGTAAGGGCC GACCGAATGC GTGGAGWULG GAATAAGTTT  746

113  GGGCCAATGT ACAAGAGAGA CAGGGCCCTG AAGCAACAGA AAAAAGCCCT  625
hFTF GGGCCAATGT ACAAGAGAGA CAGGGCCCTG AAGCAACAGA AAAAAGCCCT  796

113  CATCCGAGCC AATGGACTTA AGCTAGAAGC CATGTCTCAG GTGATCCAAG  675
hFTF CATCCGAGCC AATGGACTTA AGCTAGLLGC CATGTCTCAG GTGATCCAAG  846

113  CTATGCCCTC TGACCTGACC ATTTCCTCTG CAATTCAAAA CATCCACTCT  725
hFTF CTATGCCCTC TGACCTGACC ATTTCCTCTG CAATTCALAA CATCCACTCT  896

113  GCCTCCAAAG GCCTACCTCT GAACCATGCT GCCTTGCCTC CTACAGACTA  775
hFTF GCCTCCAAAG GCCTACCTCT WLACCATGCT GCCTTGCCTC CTACAGACTA  946

113  TGACAGAAGT CCCTTTGTAA CATCCCCCAT TAGCATGACA ATGCCCCCTC  825
hFTF TGACAGAAGT CCCTTTGTAA CATCCCCCAT TAGCLTGACA ATGC----TGC  993

113  ACGGCAGCCT GCAAGGTTAC CAAACATATG GCCACTTTCC TAGCCGGGCC  875
hFT F ACGGCAGCCT GCAAGGTTAC CAAACATATG GCCACTTTCC TAGC-        1043
     CGGGCC
```

TABLE 8-continued

```
113 = SEQ ID NO:1
hFTF = SEQ ID NO:7
```

```
113   ATCAAGTCTG AGTACCCAGA CCCCTATACC AGCTCACCCG AGTCCATAAT   925
hFTF  ATCAAGTCTG AGTACCCAGA CCCCTATACC AGCTCACCCG AGTCCATAAT  1093

113   GGGCTATTCA TATATGGATA GTTACCAGAC GAGCTCTCCA GCAAGCATCC   975
hFTF  GGGCTATTCA TATATGGATA GTTACCAGAC GAGCTCTCCA GCAAGCATCC  1143

113   CACATCTGAT ACTGGAACTT TTGAAGTGTG AGCCAGATGA GCCTCAAGTC  1025
hFTF  CACATCTGAT ACTGGAACTT TTGAAGTGTQ AGCCAGATGA GCCTCAAGTC  1193

113   CAGGCTALAA TCATGGCCTA TTTGCAGCAA GAGCAGGCTA ACCGAAGCAA  1075
hFTF  CAGGCTAAAA TCATGGCCTA TTTGCAGCAA GAGCAGGCTA ACCGAAGCAL  1243

113   GCACGAAAAG CTGAGCACCT TTGGGCTTAT GTGCAAATGA GCAGATCAAA  1125
hFTF  GCACGAAAAG CTGAGCACCT TTGGGCTTAT GTGCAAAALT GCAGATCAAA  1293

113   CTCTCTTCTC CATTGTCGAG TGGGCCAGGA GTAGTATCTT CTTCAGAGAA  1175
hFTF  CTGTCTTCTC CATTGTCGAG TGGGCCAGGA GTAGTATCTT CTTCAGAGLA  1343

113   CTTAAGGTTG ATGACCAAAT GAAGCTGCTT CAGAACTGCT GGAGTGAGCT  1225
hFTF  CTTAAGGTTG ATGACCAAAT GAAGCTGCTT CAGAACTGCT GGAGTGAGCT  1393

113   CTTAATCCTC GACCACATTT ACCGACAAGT GGTACATGGA AAGGAAGGAT  1275
hFTF  CTTAATCCTC GACCACATTT ACCGACAAGT GGTACATGGA AAGGAAGGAT  1443

113   CCATCTTCCT GGTTACTGGG CAACAAGTGG ACTATTCCAT AATAGCATCA  1325
hFTF  CCATCTTCCT GGTTACTGGG CAACAAGTGG ACTATTCCAT AATAGCATCA  1493

113   CAAGCCGGAG CCACCCTCAA CAACCTCATG AGTCATGCAC AGGAGTTAGT  1375
hFTF  CAAGCCGGAG CCACCCTCAA CAACCTCATG AGTCATGCAC AGGAGTTAGT  1543

113   GGCAAAACTT CGTTCTCTCC AGTTTGATCA ACGAGAGTTC GTATGTCTGA  1425
hFTF  GGCAAAACTT CGTTCTCTCC AGTTTGATCA ACGAGAGTTC GTATGTCTGA  1593

113   AATTCTTGGT GCTCTTTAGT TTAGATGTCA AAAACCTTGA AAACTTCCAG  1475
hFTF  AATTCTTGGT GCTCTTTAGT TTAGATGTCA AAAACCTTGA AAACTTCCAG  1643

113   CTGGTAGAAG GTGTCCAGGA ACAAGTCAAT GCCGCCCTGC TGGACTACAC  1525
hFTF  CTGGTAGAAG GTGTCCAGGA ACAAGTCAAT GCCGCCCTGC TGGACTACAC  1693

113   AATGTGTAAC TACCCGCAGC AGACAGAGAA ATTTGGACAG CTACTTCTTC  1575
hFTF  AATGTGTAAC TACCCGCAGC AGACAGAGAA ATTTGGACAG CTACTTCTTC  1743

113   GACTACCCGA AATCCGGGCC ATCAGTATGC AGGCTGAAGA ATACCTCTAC  1625
hFTF  GACTACCCGA AATCCGGGCC ATCAGTATGC AGGCTGAAGA ATACCTCTAC  1793

113   TACAAGCACC TGAACGGGGA TGTGCCCTAT AATAACCTTC TCATTGAAAT  1675
hFTF  TACAAGCACC TGAATGGGGA TGTGCCCTAT AATAACCTTC TCATTGAAAT  1843

113   GTTGCATGCC AAAAGAGCAT AAGTTACAAC CCCTAGGAGC TCTGCTTTCA  1725
hFTF  GTTGCATGCC AAAAGAGCAT AAGTTACAAC CCCTAGGAGC TCTGCTTTCA  1893

113   AAACAAAAAG AGATTGGGGG AGTGGGGAGG GGGAAGAAGA ACAGGAAGAA  1775
hFTF  AAACAAAAAG AGATTGGGGG AGTGGGGAGG GGGAAGAAGA ACAGGAAGAA  1943

113   AAAAAGTACT CTGAACTGCT CCAAGCAACG CTAATTAAAA ACTTGCTTTA  1825
hFTF  AAAAAGTACT CTGAACTGCT CCAAGTAACG CTAATTAAAA ACTTGCTTTA  1993

113   AAGATATTGA ATTTAAAAAG GCATAATAAT CAAATACTTA ATAGCAAATA  1875
hFTF  AAGATATTGA ATTTAAAAAG GCATAATAAT CAAATACT-A ATAGCAAATA  2042

113   AATGATGTAT CAGGGTATTT GTATTGCAAA CTGTGAATCA AAGGCTTCAC  1925
hFTF  AATGATGTAT CAGGGTATTT GTATTGCAAA CTGTGAATCA AA-GCTTCAC  2091

113   AGCCCCAGAG GATTCCATAT AAAAGACATT GTAATGGAGT GGATTGAACT  1975
hFTF  AGCCCCAGAG GATTCCATAT AAAAGACATT GTAATGGAGT GGATTGAACT  2141

113   CACAGATGGA TACCAACACG GTCAGAAGAA AAACGGACAG AACGGTTCTT  2025
hFTF  CACAGATGGA TACCAACACG GTCAGAAGAA AAACGGACAG AACGGTTCTT  2191

113   GTATATTTAA ACTGATCTCC ACTATGAAGA AATTTAGGAA CTAATCTTAT  2075
hFTF  GTATATTTAA ACTGATCTCC ACTATGAAGA AATTTAGQAA CTAATCTTAT  2241

113   TAATTAGGCT TATACAGCGG GGGATTTGAG CTTACAGGAT TCCTCCATGG  2125
hFTF  TAATTAGGCT TATACAGCGG GG-ATTTGAG CTTACAGGAT TCCTCCATGG  2290
```

TABLE 8-continued

```
113 = SEQ ID NO:1
hFTF = SEQ ID NO:7
```

| | | | | | | |
|---|---|---|---|---|---|---|
| 113 | TAAAGCTGAA | CTGAAACAAT | TCTCAAGAAT | GCATCAGCTG | TACCTACAAT | 2175 |
| hFTF | TAAAGCTGAA | CTGAAACAAT | TCTCAAGAAT | GCATCAGCTG | ---------- | 2330 |
| 113 | AGCCCCTCCC | TCTTCCTTTG | AAGGCCCGAG | CACCTCTGCC | CTGTGGTCAC | 2225 |
| hFTF | ---------- | ---------- | ---------- | ---------- | ---------- | 2330 |
| 113 | CGAATCTGTA | CTAAGGACCT | GTGTTCAGCC | ACACCCAGTG | GTAGCTCCAC | 2275 |
| hFTF | ---------- | ---------- | ---------- | ---------- | ---------- | 2330 |
| 113 | CAAATCATGA | ACAGCCTAAT | TTTGAGTGTC | TGTGTCTTAG | ACCTGCAAAC | 2325 |
| hFTF | ---------- | ---------- | ---------- | ---------- | ---------- | 2330 |
| 113 | AGCTAATAGG | AAATTCTATT | AATATGTTAG | CTTGCCATTT | TAAATATGTT | 2375 |
| hFTF | ---------- | ---------- | ---------- | ---------- | ---------- | 2330 |
| 113 | CTGAGGGTTG | TTTTGTCTCG | TGTTCATGAT | GTTAAGAAAA | TGCAGGCAGT | 2425 |
| hFTF | ---------- | ---------- | ---------- | ---------- | ---------- | 2330 |
| 113 | ATCCCTCATC | TTATGTAAGT | GTGAATTAAT | ATTAAGGGAA | ATGACTACAA | 2475 |
| hFTF | ---------- | ---------- | ---------- | ---------- | ---------- | 2330 |
| 113 | ACTTTCAAAG | CAAATGCTCC | ATAGCTAAAG | CAACTTAGAC | CTTATTTCTG | 2525 |
| hFTF | ---------- | ---------- | ---------- | ---------- | ---------- | 2330 |
| 113 | CTACTGTTGC | TGAAATGTGG | CTTTGGCATT | GTTGGATTTC | ATAAAAAATT | 2575 |
| hFTF | ---------- | ---------- | ---------- | ---------- | ---------- | 2330 |
| 113 | TCTGGCAGGA | AGTCTTGTTA | GTATACATCA | GTCTTTTTCA | TCATCCAAGT | 2625 |
| hFTF | ---------- | ---------- | ---------- | ---------- | ---------- | 2330 |
| 113 | TTGTAGTTCA | TTTAAAAATA | CAACATTAAA | CACATTTTGC | TAGGATGTCA | 2675 |
| hFTF | ---------- | ---------- | ---------- | ---------- | ---------- | 2330 |
| 113 | AATAGTCACA | GTTCTAAGTA | GTTGGAAACA | AAATTGACGC | ATGTTAATCT | 2725 |
| hFTF | ---------- | ---------- | ---------- | ---------- | ---------- | 2330 |
| 113 | ATGCAAAGAG | AAAGGAAAGG | ATGAGGTGAT | GTATTGACTC | AAGGTTCATT | 2775 |
| hFTF | ---------- | ---------- | ---------- | ---------- | ---------- | 2330 |
| 113 | CTTGCTGCAA | TTGAACATCC | TCAAGAGTTG | GGATGGAAAT | GGTGATTTTT | 2825 |
| hFTF | ---------- | ---------- | ---------- | ---------- | ---------- | 2330 |
| 113 | ACATGTGTCC | TGGAAAGATA | TTAAAGTAAT | TCAAATCTTC | CCCAAAGGGG | 2875 |
| hFTF | ---------- | ---------- | ---------- | ---------- | ---------- | 2330 |
| 113 | AAAGGAAGAG | AGTGATACTG | ACCTTTTTAA | GTCATAGACC | AAAGTCTGCT | 2925 |
| hFTF | ---------- | ---------- | ---------- | ---------- | ---------- | 2330 |
| 113 | GTAGAACAAA | TATGGGAGGA | CAAAGAATCG | CAAATTCTTC | AAATGACTAT | 2975 |
| hFTF | ---------- | ---------- | ---------- | ---------- | ---------- | 2330 |
| 113 | TATCAGTATT | ATTAACATGC | GATGCCACAG | GTATGAAAGT | CTTGCCTTAT | 3025 |
| hFTF | ---------- | ---------- | ---------- | ---------- | ---------- | 2330 |
| 113 | TTCACAATTT | TAAAAGGTAG | CTGTGCAGAT | GTGGATCAAC | ATTTGTTTAA | 3075 |
| hFTF | ---------- | ---------- | ---------- | ---------- | ---------- | 2330 |
| 113 | AATAAAGTAT | TAATACTTTA | AAGTCAAAAA | AAAAAAAAA | | 3115 |
| hFTF | ---------- | ---------- | ---------- | ---------- | | 2330 |

What is claimed is:

1. A recombinant polynucleotide comprising a cDNA which comprises a coding region encoding a polypeptide comprising: (a) SEQ ID NO:2, 4, or 6, or (b) at least ten contiguous amino acid residues of SEQ ID NO:2 comprising at least one sequence selected from the group consisting of amino acid residues 1–10, 11–15 and 16–21 of SEQ ID NO:2, or (c) at least ten contiguous amino acid residues of SEQ ID NO:6 comprising at least one sequence selected from the group consisting of amino acid residues 3–10, 13–22 and 30–38 of SEQ ID NO:6, wherein said cDNA is flanked by a sequence other than that which it is joined to on a natural chromosome.

2. A polynucleotide according to claim 1, said polypeptide comprising at least ten contiguous amino acid residues of SEQ ID NO:2 comprising at least one sequence selected from the group consisting of amino acid residues 1–10, 11–15, and 16–21, or at least ten contiguous amino acid residues of SEQ ID NO:6 comprising at least one sequence selected from the group consisting of amino acid residues 3–10, 13–22 and 30–38 of SEQ ID NO:6.

3. A polynucleotide according to claim 1, said polypeptide comprising at least one sequence selected from the group consisting of amino acid residues 1–10, 4–15, 8–20, 12–25, 15–30, 19–32, 20–29 and 200–211 of SEQ ID NO:2.

4. A polynucleotide according to claim 1, said polypeptide comprising at least one sequence selected from the group consisting of amino acid residues 33–123, 242–333 and 383–405 of SEQ ID NO:2.

5. A recombinant polynucleotide comprising a coding region encoding a polypeptide comprising at least ten contiguous amino acid residues of SEQ ID NO:4 comprising amino acid residues 150–159 of SEQ ID NO:4.

6. A polynucleotide according to claim 1, said polypeptide, comprising at least 16 contiguous amino acid residues of SEQ ID NO:2 comprising at least one sequence selected from the group consisting of amino acid residues 1–10, 11–15, 16–21, and 204–207 of SEQ ID NO:2.

7. A polynucleotide according to claim 1, said polypeptide comprising at least 32 contiguous amino acid residues of SEQ ID NO:2 comprising at least one sequence selected from the group consisting of amino acid residues 1–10, 11–15, 16–21, 204–207 and 299–307 of SEQ ID NO:2.

8. A polynucleotide according to claim 1, said polypeptide comprising at least 64 contiguous amino acid residues of SEQ ID NO:2 comprising at least one sequence selected from the group consisting of amino acid residues 1–10, 11–15, 16–21, 204–207 and 299–307 of SEQ ID NO:2.

9. A polynucleotide according to claim 1, said polypeptide comprising at least 16 contiguous amino acid residues of SEQ ID NO:4 comprising amino acid residue 154 of SEQ ID NO:4.

10. A recombinant polynucleotide comprising a cDNA which comprises a coding region encoding a polynucleotide comprising at least 32 contiguous amino acid residues of SEQ ID NO:4 comprising amino acid residue 154 of SEQ ID NO:4, wherein said cDNA is flanked by a sequence other than that which it is joined to on a natural chromosome.

11. A polynucleotide according to claim 10, said polypeptide comprising at least 64 contiguous amino acid residues of SEQ ID NO:4 comprising amino acid residue 154 of SEQ ID NO:4.

12. A polynucleotide according to claim 1, said polypeptide comprising at least 16 contiguous amino acid residues of SEQ ID NO:6 comprising at least one sequence selected from the group consisting of amino acid residues 3–10, 13–22 and 30–38 of SEQ ID NO:6.

13. A polynucleotide according to claim 1, said polypeptide comprising at least 32 contiguous amino acid residues of SEQ ID NO:6 comprising at least one sequence selected from the group consisting of amino acid residues 3–10, 13–22 and 30–38 of SEQ ID NO:6.

14. A polynucleotide according to claim 1, said polypeptide comprising at least 64 contiguous amino acid residues of SEQ ID NO:6 comprising at least one sequence selected from the group consisting of amino acid residues 3–10, 13–22 and 30–38 of SEQ ID NO:6.

15. A polynucleotide according to claim 1, wherein said polypeptide specifically binds the CYP7 gene promoter.

16. A method of screening comprising the steps of:
translating a polynucleotide according to claim 1 to produce the polypeptide;
incubating in vitro or in culture a mixture comprising:
the polypeptide,
a binding target of said polypeptide, and
a candidate agent,
under conditions whereby, but for the presence of said agent, said polypeptide specifically binds said binding target at a reference affinity; and
detecting the binding affinity of said polypeptide to said binding target to determine an agent-biased affinity, wherein a difference between the agent-biased affinity and the reference affinity indicates that said agent modulates the binding of said polypeptide to said binding target.

17. A method according to claim 16, wherein the binding target is a nucleic acid comprising a CYP7 promoter sequence sufficient to specifically bind the polypeptide.

18. A method of screening, said method comprising the steps of: translating a polynucleotide according to claim 1 to produce the polypeptide; incubating in vitro or in culture a mixture comprising the polypeptide and a candidate agent under conditions whereby said agent specifically binds said polypeptide; and detecting the specifically bound agent.

19. A recombinant polynucleotide comprising a cDNA which comprises a sequence selected from, (a) the group consisting of SEQ ID NO:1, 3 and 5 or (b) the group consisting of nucleotides 1–26, 52–62, 1630–1650, 1790–1810, 1855–1875, 1910–1925, 2566–2586, and 2666–2686 of SEQ ID NO:1, wherein said cDNA is flanked by a sequence other than that which it is joined to on a natural chromosome.

20. A recombinant polynucleotide according to claim 19 comprising a sequence selected from the group consisting of SEQ ID NO:1, 3 and 5.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 3115 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 210..1694

(xi) SEQUENCE DESCRIPTION: SEQ ID NO:1:

```
GAAAAAGTA  CAGAGTCCAG  GGAAAAGACT  TGCTTGTAAC  TTTATGAATT  CTGGATTTTT    60

TTTTTTCCTT  TGCTTTTTCT  TAACTTTCAC  TAAGGGTTAC  TGTAGTCTGA  TGTGTCCTTC   120

CCAAGGCCAC  GAAATTTGAC  AAGCTGCACT  TTTCTTTTGC  TCAATGATTT  CTGCTTTAAG   180
```

```
CCAAAGAACT GCCTATAATT TCACTAAGA ATG TCT TCT AAT TCA GAT ACT GGG        233
                                Met Ser Ser Asn Ser Asp Thr Gly
                                 1               5

GAT TTA CAA GAG TCT TTA AAG CAC GGA CTT ACA CCT ATT GTG TCT CAA        281
Asp Leu Gln Glu Ser Leu Lys His Gly Leu Thr Pro Ile Val Ser Gln
     10              15                  20

TTT AAA ATG GTG AAT TAC TCC TAT GAT GAA GAT CTG GAA GAG CTT TGT        329
Phe Lys Met Val Asn Tyr Ser Tyr Asp Glu Asp Leu Glu Glu Leu Cys
 25              30                  35                      40

CCC GTG TGT GGA GAT AAA GTG TCT GGG TAC CAT TAT GGG CTC CTC ACC        377
Pro Val Cys Gly Asp Lys Val Ser Gly Tyr His Tyr Gly Leu Leu Thr
                 45                  50                  55

TGT GAA AGC TGC AAG GGA TTT TTT AAG CGA ACA GTC CAA AAT AAT AAA        425
Cys Glu Ser Cys Lys Gly Phe Phe Lys Arg Thr Val Gln Asn Asn Lys
             60                  65                  70

AGG TAC ACA TGT ATA GAA AAC CAG AAC TGC CAA ATT GAC AAA ACA CAG        473
Arg Tyr Thr Cys Ile Glu Asn Gln Asn Cys Gln Ile Asp Lys Thr Gln
         75                  80                  85

AGA AAG CGT TGT CCT TAC TGT CGT TTT CAA AAA TGT CTA AGT GTT GGA        521
Arg Lys Arg Cys Pro Tyr Cys Arg Phe Gln Lys Cys Leu Ser Val Gly
     90                  95                 100

ATG AAG CTA GAA GCT GTA AGG GCC GAC CGA ATG CGT GGA GGA AGG AAT        569
Met Lys Leu Glu Ala Val Arg Ala Asp Arg Met Arg Gly Gly Arg Asn
105             110                 115                 120

AAG TTT GGG CCA ATG TAC AAG AGA GAC AGG GCC CTG AAG CAA CAG AAA        617
Lys Phe Gly Pro Met Tyr Lys Arg Asp Arg Ala Leu Lys Gln Gln Lys
                125                 130                 135

AAA GCC CTC ATC CGA GCC AAT GGA CTT AAG CTA GAA GCC ATG TCT CAG        665
Lys Ala Leu Ile Arg Ala Asn Gly Leu Lys Leu Glu Ala Met Ser Gln
             140                 145                 150

GTG ATC CAA GCT ATG CCC TCT GAC CTG ACC ATT TCC TCT GCA ATT CAA        713
Val Ile Gln Ala Met Pro Ser Asp Leu Thr Ile Ser Ser Ala Ile Gln
         155                 160                 165

AAC ATC CAC TCT GCC TCC AAA GGC CTA CCT CTG AAC CAT GCT GCC TTG        761
Asn Ile His Ser Ala Ser Lys Gly Leu Pro Leu Asn His Ala Ala Leu
     170                 175                 180

CCT CCT ACA GAC TAT GAC AGA AGT CCC TTT GTA ACA TCC CCC ATT AGC        809
Pro Pro Thr Asp Tyr Asp Arg Ser Pro Phe Val Thr Ser Pro Ile Ser
185                 190                 195                 200

ATG ACA ATG CCC CCT CAC GGC AGC CTG CAA GGT TAC CAA ACA TAT GGC        857
Met Thr Met Pro Pro His Gly Ser Leu Gln Gly Tyr Gln Thr Tyr Gly
                205                 210                 215

CAC TTT CCT AGC CGG GCC ATC AAG TCT GAG TAC CCA GAC CCC TAT ACC        905
His Phe Pro Ser Arg Ala Ile Lys Ser Glu Tyr Pro Asp Pro Tyr Thr
                220                 225                 230

AGC TCA CCC GAG TCC ATA ATG GGC TAT TCA TAT ATG GAT AGT TAC CAG        953
Ser Ser Pro Glu Ser Ile Met Gly Tyr Ser Tyr Met Asp Ser Tyr Gln
            235                 240                 245

ACG AGC TCT CCA GCA AGC ATC CCA CAT CTG ATA CTG GAA CTT TTG AAG       1001
Thr Ser Ser Pro Ala Ser Ile Pro His Leu Ile Leu Glu Leu Leu Lys
        250                 255                 260

TGT GAG CCA GAT GAG CCT CAA GTC CAG GCT AAA ATC ATG GCC TAT TTG       1049
Cys Glu Pro Asp Glu Pro Gln Val Gln Ala Lys Ile Met Ala Tyr Leu
265                 270                 275                 280

CAG CAA GAG CAG GCT AAC CGA AGC AAG CAC GAA AAG CTG AGC ACC TTT       1097
Gln Gln Glu Gln Ala Asn Arg Ser Lys His Glu Lys Leu Ser Thr Phe
                285                 290                 295

GGG CTT ATG TGC AAA ATG GCA GAT CAA ACT CTC TTC TCC ATT GTC GAG       1145
Gly Leu Met Cys Lys Met Ala Asp Gln Thr Leu Phe Ser Ile Val Glu
```

```
                    300                 305                 310
TGG GCC AGG AGT AGT ATC TTC TTC AGA GAA CTT AAG GTT GAT GAC CAA    1193
Trp Ala Arg Ser Ser Ile Phe Phe Arg Glu Leu Lys Val Asp Asp Gln
        315                 320                 325

ATG AAG CTG CTT CAG AAC TGC TGG AGT GAG CTC TTA ATC CTC GAC CAC    1241
Met Lys Leu Leu Gln Asn Cys Trp Ser Glu Leu Leu Ile Leu Asp His
    330                 335                 340

ATT TAC CGA CAA GTG GTA CAT GGA AAG GAA GGA TCC ATC TTC CTG GTT    1289
Ile Tyr Arg Gln Val Val His Gly Lys Glu Gly Ser Ile Phe Leu Val
345                 350                 355                 360

ACT GGG CAA CAA GTG GAC TAT TCC ATA ATA GCA TCA CAA GCC GGA GCC    1337
Thr Gly Gln Gln Val Asp Tyr Ser Ile Ile Ala Ser Gln Ala Gly Ala
                365                 370                 375

ACC CTC AAC AAC CTC ATG AGT CAT GCA CAG GAG TTA GTG GCA AAA CTT    1385
Thr Leu Asn Asn Leu Met Ser His Ala Gln Glu Leu Val Ala Lys Leu
            380                 385                 390

CGT TCT CTC CAG TTT GAT CAA CGA GAG TTC GTA TGT CTG AAA TTC TTG    1433
Arg Ser Leu Gln Phe Asp Gln Arg Glu Phe Val Cys Leu Lys Phe Leu
        395                 400                 405

GTG CTC TTT AGT TTA GAT GTC AAA AAC CTT GAA AAC TTC CAG CTG GTA    1481
Val Leu Phe Ser Leu Asp Val Lys Asn Leu Glu Asn Phe Gln Leu Val
    410                 415                 420

GAA GGT GTC CAG GAA CAA GTC AAT GCC GCC CTG CTG GAC TAC ACA ATG    1529
Glu Gly Val Gln Glu Gln Val Asn Ala Ala Leu Leu Asp Tyr Thr Met
425                 430                 435                 440

TGT AAC TAC CCG CAG CAG ACA GAG AAA TTT GGA CAG CTA CTT CTT CGA    1577
Cys Asn Tyr Pro Gln Gln Thr Glu Lys Phe Gly Gln Leu Leu Leu Arg
                445                 450                 455

CTA CCC GAA ATC CGG GCC ATC AGT ATG CAG GCT GAA GAA TAC CTC TAC    1625
Leu Pro Glu Ile Arg Ala Ile Ser Met Gln Ala Glu Glu Tyr Leu Tyr
            460                 465                 470

TAC AAG CAC CTG AAC GGG GAT GTG CCC TAT AAT AAC CTT CTC ATT GAA    1673
Tyr Lys His Leu Asn Gly Asp Val Pro Tyr Asn Asn Leu Leu Ile Glu
        475                 480                 485

ATG TTG CAT GCC AAA AGA GCA TAAGTTACAA CCCCTAGGAG CTCTGCTTTC        1724
Met Leu His Ala Lys Arg Ala
    490                 495

AAAACAAAAA GAGATTGGGG GAGTGGGGAG GGGGAAGAAG AACAGGAAGA AAAAAAGTAC   1784

TCTGAACTGC TCCAAGCAAC GCTAATTAAA AACTTGCTTT AAAGATATTG AATTTAAAAA   1844

GGCATAATAA TCAAATACTT AATAGCAAAT AAATGATGTA TCAGGGTATT TGTATTGCAA   1904

ACTGTGAATC AAAGGCTTCA CAGCCCCAGA GGATTCCATA TAAAAGACAT TGTAATGGAG   1964

TGGATTGAAC TCACAGATGG ATACCAACAC GGTCAGAAGA AAAACGGACA GAACGGTTCT   2024

TGTATATTTA AACTGATCTC CACTATGAAG AAATTTAGGA ACTAATCTTA TTAATTAGGC   2084

TTATACAGCG GGGGATTTGA GCTTACAGGA TTCCTCCATG GTAAAGCTGA ACTGAAACAA   2144

TTCTCAAGAA TGCATCAGCT GTACCTACAA TAGCCCCTCC CTCTTCCTTT GAAGGCCCGA   2204

GCACCTCTGC CCTGTGGTCA CCGAATCTGT ACTAAGGACC TGTGTTCAGC CACACCCAGT   2264

GGTAGCTCCA CCAAATCATG AACAGCCTAA TTTTGAGTGT CTGTGTCTTA GACCTGCAAA   2324

CAGCTAATAG GAAATTCTAT TAATATGTTA GCTTGCCATT TTAAATATGT TCTGAGGGTT   2384

GTTTTGTCTC GTGTTCATGA TGTTAAGAAA ATGCAGGCAG TATCCCTCAT CTTATGTAAG   2444

TGTGAATTAA TATTAAGGGA AATGACTACA AACTTTCAAA GCAAATGCTC CATAGCTAAA   2504

GCAACTTAGA CCTTATTTCT GCTACTGTTG CTGAAATGTG GCTTTGGCAT TGTTGGATTT   2564

CATAAAAAAT TTCTGGCAGG AAGTCTTGTT AGTATACATC AGTCTTTTTC ATCATCCAAG   2624
```

```
TTTGTAGTTC ATTTAAAAAT ACAACATTAA ACACATTTTG CTAGGATGTC AAATAGTCAC      2684

AGTTCTAAGT AGTGGAAAC AAAATTGACG CATGTTAATC TATGCAAAGA GAAAGGAAAG      2744

GATGAGGTGA TGTATTGACT CAAGGTTCAT TCTTGCTGCA ATTGAACATC CTCAAGAGTT      2804

GGGATGGAAA TGGTGATTTT TACATGTGTC CTGGAAAGAT ATTAAAGTAA TTCAAATCTT      2864

CCCCAAAGGG GAAAGGAAGA GAGTGATACT GACCTTTTTA AGTCATAGAC CAAAGTCTGC      2924

TGTAGAACAA ATATGGGAGG ACAAAGAATC GCAAATTCTT CAAATGACTA TTATCAGTAT      2984

TATTAACATG CGATGCCACA GGTATGAAAG TCTTGCCTTA TTTCACAATT TTAAAAGGTA      3044

GCTGTGCAGA TGTGGATCAA CATTTGTTTA AATAAAGTA TTAATACTTT AAAGTCAAAA      3104

AAAAAAAAA A                                                            3115

(2) INFORMATION FOR SEQ ID NO:2:

(i) SEQUENCE CHARACTERISTICS:
        (A) LENGTH: 495 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ser Asn Ser Asp Thr Gly Asp Leu Gln Glu Ser Leu Lys His
  1               5                  10                  15

Gly Leu Thr Pro Ile Val Ser Gln Phe Lys Met Val Asn Tyr Ser Tyr
             20                  25                  30

Asp Glu Asp Leu Glu Glu Leu Cys Pro Val Cys Gly Asp Lys Val Ser
         35                  40                  45

Gly Tyr His Tyr Gly Leu Leu Thr Cys Glu Ser Cys Lys Gly Phe Phe
     50                  55                  60

Lys Arg Thr Val Gln Asn Asn Lys Arg Tyr Thr Cys Ile Glu Asn Gln
 65                  70                  75                  80

Asn Cys Gln Ile Asp Lys Thr Gln Arg Lys Arg Cys Pro Tyr Cys Arg
                 85                  90                  95

Phe Gln Lys Cys Leu Ser Val Gly Met Lys Leu Glu Ala Val Arg Ala
            100                 105                 110

Asp Arg Met Arg Gly Gly Arg Asn Lys Phe Gly Pro Met Tyr Lys Arg
        115                 120                 125

Asp Arg Ala Leu Lys Gln Gln Lys Lys Ala Leu Ile Arg Ala Asn Gly
    130                 135                 140

Leu Lys Leu Glu Ala Met Ser Gln Val Ile Gln Ala Met Pro Ser Asp
145                 150                 155                 160

Leu Thr Ile Ser Ser Ala Ile Gln Asn Ile His Ser Ala Ser Lys Gly
                165                 170                 175

Leu Pro Leu Asn His Ala Ala Leu Pro Pro Thr Asp Tyr Asp Arg Ser
            180                 185                 190

Pro Phe Val Thr Ser Pro Ile Ser Met Thr Met Pro Pro His Gly Ser
        195                 200                 205

Leu Gln Gly Tyr Gln Thr Tyr Gly His Phe Pro Ser Arg Ala Ile Lys
    210                 215                 220

Ser Glu Tyr Pro Asp Pro Tyr Thr Ser Ser Pro Glu Ser Ile Met Gly
225                 230                 235                 240

Tyr Ser Tyr Met Asp Ser Tyr Gln Thr Ser Ser Pro Ala Ser Ile Pro
                245                 250                 255
```

```
His Leu Ile Leu Glu Leu Leu Lys Cys Glu Pro Asp Glu Pro Gln Val
            260                 265                 270

Gln Ala Lys Ile Met Ala Tyr Leu Gln Gln Glu Gln Ala Asn Arg Ser
        275                 280                 285

Lys His Glu Lys Leu Ser Thr Phe Gly Leu Met Cys Lys Met Ala Asp
    290                 295                 300

Gln Thr Leu Phe Ser Ile Val Glu Trp Ala Arg Ser Ser Ile Phe Phe
305                 310                 315                 320

Arg Glu Leu Lys Val Asp Asp Gln Met Lys Leu Leu Gln Asn Cys Trp
                325                 330                 335

Ser Glu Leu Leu Ile Leu Asp His Ile Tyr Arg Gln Val Val His Gly
            340                 345                 350

Lys Glu Gly Ser Ile Phe Leu Val Thr Gly Gln Gln Val Asp Tyr Ser
        355                 360                 365

Ile Ile Ala Ser Gln Ala Gly Ala Thr Leu Asn Asn Leu Met Ser His
370                 375                 380

Ala Gln Glu Leu Val Ala Lys Leu Arg Ser Leu Gln Phe Asp Gln Arg
385                 390                 395                 400

Glu Phe Val Cys Leu Lys Phe Leu Val Leu Phe Ser Leu Asp Val Lys
                405                 410                 415

Asn Leu Glu Asn Phe Gln Leu Val Glu Gly Val Gln Glu Gln Val Asn
            420                 425                 430

Ala Ala Leu Leu Asp Tyr Thr Met Cys Asn Tyr Pro Gln Gln Thr Glu
        435                 440                 445

Lys Phe Gly Gln Leu Leu Leu Arg Leu Pro Glu Ile Arg Ala Ile Ser
    450                 455                 460

Met Gln Ala Glu Glu Tyr Leu Tyr Tyr Lys His Leu Asn Gly Asp Val
465                 470                 475                 480

Pro Tyr Asn Asn Leu Leu Ile Glu Met Leu His Ala Lys Arg Ala
                485                 490                 495
```

(2) INFORMATION FOR SEQ ID NO:3:

(i) SEQUENCE CHARACTERISTICS:
        (A) LENGTH: 1245 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 202..1170

(xi) SEQUENCE DESCRIPTION: SEQ ID NO:3:

```
CGGCCGCGTC GACGGAAAGA CTTGCTTGTA ACTTTATGAA TTCTGGATTT TTTTTTTTCC    60

TTTGCTTTTT CTTAACTTTC ACTAAGGGTT ACTGTAGTCT GATGTGTCCT TCCCAAGGCC   120

ACGAAATTTG ACAAGCTGCA CTTTTCTTTT GCTCAATGAT TTCTGCTTTA AGCCAAAGAA   180

CTGCCTATAA TTTCACTAAG A ATG TCT TCT AAT TCA GAT ACT GGG GAT TTA    231
                       Met Ser Ser Asn Ser Asp Thr Gly Asp Leu
                                           500                 505

CAA GAG TCT TTA AAG CAC GGA CTT ACA CCT ATT GTG TCT CAA TTT AAA    279
Gln Glu Ser Leu Lys His Gly Leu Thr Pro Ile Val Ser Gln Phe Lys
            510                 515                 520

ATG GTG AAT TAC TCC TAT GAT GAA GAT CTG GAA GAG CTT TGT CCC GTG    327
Met Val Asn Tyr Ser Tyr Asp Glu Asp Leu Glu Glu Leu Cys Pro Val
        525                 530                 535
```

-continued

```
TGT GGA GAT AAA GTG TCT GGG TAC CAT TAT GGG CTC CTC ACC TGT GAA        375
Cys Gly Asp Lys Val Ser Gly Tyr His Tyr Gly Leu Leu Thr Cys Glu
            540                 545                 550

AGC TGC AAG GGA TTT TTT AAG CGA ACA GTC CAA AAT AAT AAA AGG TAC        423
Ser Cys Lys Gly Phe Phe Lys Arg Thr Val Gln Asn Asn Lys Arg Tyr
        555                 560                 565

ACA TGT ATA GAA AAC CAG AAC TGC CAA ATT GAC AAA ACA CAG AGA AAG        471
Thr Cys Ile Glu Asn Gln Asn Cys Gln Ile Asp Lys Thr Gln Arg Lys
570                 575                 580                 585

CGT TGT CCT TAC TGT CGT TTT CAA AAA TGT CTA AGT GTT GGA ATG AAG        519
Arg Cys Pro Tyr Cys Arg Phe Gln Lys Cys Leu Ser Val Gly Met Lys
                590                 595                 600

CTA GAA GCT GTA AGG GCC GAC CGA ATG CGT GGA GGA AGG AAT AAG TTT        567
Leu Glu Ala Val Arg Ala Asp Arg Met Arg Gly Gly Arg Asn Lys Phe
            605                 610                 615

GGG CCA ATG TAC AAG AGA GAC AGG GCC CTG AAG CAA CAG AAA AAA GCC        615
Gly Pro Met Tyr Lys Arg Asp Arg Ala Leu Lys Gln Gln Lys Lys Ala
        620                 625                 630

CTC ATC CGA GCC AAT GGA CTT AAG CTA GAA GCC ATG TCT CAG GTT GAT        663
Leu Ile Arg Ala Asn Gly Leu Lys Leu Glu Ala Met Ser Gln Val Asp
635                 640                 645

GAC CAA ATG AAG CTG CTT CAG AAC TGC TGG AGT GAG CTC TTA ATC CTC        711
Asp Gln Met Lys Leu Leu Gln Asn Cys Trp Ser Glu Leu Leu Ile Leu
650                 655                 660                 665

GAC CAC ATT TAC CGA CAA GTG GTA CAT GGA AAG GAA GGA TCC ATC TTC        759
Asp His Ile Tyr Arg Gln Val Val His Gly Lys Glu Gly Ser Ile Phe
                670                 675                 680

CTG GTT ACT GGG CAA CAA GTG GAC TAT TCC ATA ATA GCA TCA CAA GCC        807
Leu Val Thr Gly Gln Gln Val Asp Tyr Ser Ile Ile Ala Ser Gln Ala
            685                 690                 695

GGA GCC ACC CTC AAC AAC CTC ATG AGT CAT GCA CAG GAG TTA GTG GCA        855
Gly Ala Thr Leu Asn Asn Leu Met Ser His Ala Gln Glu Leu Val Ala
        700                 705                 710

AAA CTT CGT TCT CTC CAG TTT GAT CAA CGA GAG TTC GTA TGT CTG AAA        903
Lys Leu Arg Ser Leu Gln Phe Asp Gln Arg Glu Phe Val Cys Leu Lys
715                 720                 725

TTC TTG GTG CTC TTT AGT TTA GAT GTC AAA AAC CTT GAA AAC TTC CAG        951
Phe Leu Val Leu Phe Ser Leu Asp Val Lys Asn Leu Glu Asn Phe Gln
730                 735                 740                 745

CTG GTA GAA GGT GTC CAG GAA CAA GTC AAT GCC GCC CTG CTG GAC TAC        999
Leu Val Glu Gly Val Gln Glu Gln Val Asn Ala Ala Leu Leu Asp Tyr
                750                 755                 760

ACA ATG TGT AAC TAC CCG CAG CAG ACA GAG AAA TTT CGA CAG CTA CTT       1047
Thr Met Cys Asn Tyr Pro Gln Gln Thr Glu Lys Phe Arg Gln Leu Leu
            765                 770                 775

CTT CGA CTA CCC GAA ATC CGG GCC ATC AGT ATG CAG GCT GAA GAA TAC       1095
Leu Arg Leu Pro Glu Ile Arg Ala Ile Ser Met Gln Ala Glu Glu Tyr
        780                 785                 790

CTC TAC TAC AAG CAC CTG AAC GGG GAT GTG CCC TAT AAT AAC CTT CTC       1143
Leu Tyr Tyr Lys His Leu Asn Gly Asp Val Pro Tyr Asn Asn Leu Leu
795                 800                 805

ATT GAA ATG TTG CAT GCC AAA AGA GCA TAAGTTACAA CCCCTAGGAG             1190
Ile Glu Met Leu His Ala Lys Arg Ala
810                 815

CTCTGCTTTC AAAACAAAAA GAGATTGGGG GAGTGGGGAG GGGGAAGAAG AACAG          1245
```

(2) INFORMATION FOR SEQ ID NO:4:

(i) SEQUENCE CHARACTERISTICS:

(A) LENGTH: 323 amino acids
(B) TYPE: amino acid
(D) TOPOLOGY: linear (ii) MOLECULE TYPE: protein (xi) SEQUENCE DESCRIPTION: SEQ ID NO:4:

```
Met Ser Ser Asn Ser Asp Thr Gly Asp Leu Gln Glu Ser Leu Lys His
 1               5                  10                  15

Gly Leu Thr Pro Ile Val Ser Gln Phe Lys Met Val Asn Tyr Ser Tyr
                20                  25                  30

Asp Glu Asp Leu Glu Glu Leu Cys Pro Val Cys Gly Asp Lys Val Ser
            35                  40                  45

Gly Tyr His Tyr Gly Leu Leu Thr Cys Glu Ser Cys Lys Gly Phe Phe
    50                  55                  60

Lys Arg Thr Val Gln Asn Asn Lys Arg Tyr Thr Cys Ile Glu Asn Gln
65                  70                  75                  80

Asn Cys Gln Ile Asp Lys Thr Gln Arg Lys Arg Cys Pro Tyr Cys Arg
                85                  90                  95

Phe Gln Lys Cys Leu Ser Val Gly Met Lys Leu Glu Ala Val Arg Ala
                100                 105                 110

Asp Arg Met Arg Gly Gly Arg Asn Lys Phe Gly Pro Met Tyr Lys Arg
            115                 120                 125

Asp Arg Ala Leu Lys Gln Gln Lys Lys Ala Leu Ile Arg Ala Asn Gly
    130                 135                 140

Leu Lys Leu Glu Ala Met Ser Gln Val Asp Asp Gln Met Lys Leu Leu
145                 150                 155                 160

Gln Asn Cys Trp Ser Glu Leu Leu Ile Leu Asp His Ile Tyr Arg Gln
                165                 170                 175

Val Val His Gly Lys Glu Gly Ser Ile Phe Leu Val Thr Gly Gln Gln
            180                 185                 190

Val Asp Tyr Ser Ile Ile Ala Ser Gln Ala Gly Ala Thr Leu Asn Asn
    195                 200                 205

Leu Met Ser His Ala Gln Glu Leu Val Ala Lys Leu Arg Ser Leu Gln
210                 215                 220

Phe Asp Gln Arg Glu Phe Val Cys Leu Lys Phe Leu Val Leu Phe Ser
225                 230                 235                 240

Leu Asp Val Lys Asn Leu Glu Asn Phe Gln Leu Val Glu Gly Val Gln
                245                 250                 255

Glu Gln Val Asn Ala Ala Leu Leu Asp Tyr Thr Met Cys Asn Tyr Pro
            260                 265                 270

Gln Gln Thr Glu Lys Phe Arg Gln Leu Leu Leu Arg Leu Pro Glu Ile
    275                 280                 285

Arg Ala Ile Ser Met Gln Ala Glu Glu Tyr Leu Tyr Tyr Lys His Leu
290                 295                 300

Asn Gly Asp Val Pro Tyr Asn Asn Leu Leu Ile Glu Met Leu His Ala
305                 310                 315                 320

Lys Arg Ala
```

(2) INFORMATION FOR SEQ ID NO:5:

(i) SEQUENCE CHARACTERISTICS:
(A) LENGTH: 3251 base pairs
(B) TYPE: nucleic acid
(C) STRANDEDNESS: double
(D) TOPOLOGY: linear (ii) MOLECULE TYPE: cDNA (ix) FEATURE:
    (A) NAME/KEY: CDS
    (B) LOCATION: 208..1830

(xi) SEQUENCE DESCRIPTION: SEQ ID NO:5:

```
CGCGGCCGCG TCGACCAGGG AAAAGACTTG CTTGTAACTT TATGAATTCT GGATTTTTTT      60

TTTTCCTTTG CTTTTTCTTA ACTTTCACTA AGGGTTACTG TAGTCTGATG TGTCCTTCCC     120

AAGGCCACGA AATTTGACAA GCTGCACTTT TCTTTTGCTC AATGATTTCT GCTTTAAGCC     180

AAAGAACTGC CTATAATTTC ACTAAGA ATG TCT TCT AAT TCA GAT ACT GGG         231
                             Met Ser Ser Asn Ser Asp Thr Gly
                             325                 330

GAT TTA CAA GAG TCT TTA AAG CAC GGA CTT ACA CCT ATT GGT GCT GGG       279
Asp Leu Gln Glu Ser Leu Lys His Gly Leu Thr Pro Ile Gly Ala Gly
            335                 340                 345

CTT CCG GAC CGA CAC GGA TCC CCC ATC CCC GCC CGC GGT CGC CTT GTC       327
Leu Pro Asp Arg His Gly Ser Pro Ile Pro Ala Arg Gly Arg Leu Val
        350                 355                 360

ATG CTG CCC AAA GTG GAG ACG GAA GCC CTG GGA CTG GCT CGA TCG CAT       375
Met Leu Pro Lys Val Glu Thr Glu Ala Leu Gly Leu Ala Arg Ser His
    365                 370                 375

GGG GAA CAG GGC CAG ATG CCG GAA AAC ATG CAA GTG TCT CAA TTT AAA       423
Gly Glu Gln Gly Gln Met Pro Glu Asn Met Gln Val Ser Gln Phe Lys
380                 385                 390                 395

ATG GTG AAT TAC TCC TAT GAT GAA GAT CTG GAA GAA CTT TGT CCC GTG       471
Met Val Asn Tyr Ser Tyr Asp Glu Asp Leu Glu Glu Leu Cys Pro Val
                400                 405                 410

TGT GGA GAT AAA GTG TCT GGG TAC CAT TAT GGG CTC CTC ACC TGT GAA       519
Cys Gly Asp Lys Val Ser Gly Tyr His Tyr Gly Leu Leu Thr Cys Glu
            415                 420                 425

AGC TGC AAG GGA TTT TTT AAG CGA ACA GTC CAA AAT AAT AAA AGG TAC       567
Ser Cys Lys Gly Phe Phe Lys Arg Thr Val Gln Asn Asn Lys Arg Tyr
        430                 435                 440

ACA TGT ATA GAA AAC CAG AAC TGC CAA ATT GAC AAA ACA CAG AGA AAG       615
Thr Cys Ile Glu Asn Gln Asn Cys Gln Ile Asp Lys Thr Gln Arg Lys
    445                 450                 455

CGT TGT CCT TAC TGT CGT TTT CAA AAA TGT CTA AGT GTT GGA ATG AAG       663
Arg Cys Pro Tyr Cys Arg Phe Gln Lys Cys Leu Ser Val Gly Met Lys
460                 465                 470                 475

CTA GAA GCT GTA AGG GCC GAC CGA ATG CGT GGA GGA AGG AAT AAG TTT       711
Leu Glu Ala Val Arg Ala Asp Arg Met Arg Gly Gly Arg Asn Lys Phe
                480                 485                 490

GGG CCA ATG TAC AAG AGA GAC AGG GCC CTG AAG CAA CAG AAA AAA GCC       759
Gly Pro Met Tyr Lys Arg Asp Arg Ala Leu Lys Gln Gln Lys Lys Ala
            495                 500                 505

CTC ATC CGA GCC AAT GGA CTT AAG CTA GAA GCC ATG TCT CAG GTG ATC       807
Leu Ile Arg Ala Asn Gly Leu Lys Leu Glu Ala Met Ser Gln Val Ile
        510                 515                 520

CAA GCT ATG CCC TCT GAC CTG ACC ATT TCC TCT GCA ATT CAA AAC ATC       855
Gln Ala Met Pro Ser Asp Leu Thr Ile Ser Ser Ala Ile Gln Asn Ile
    525                 530                 535

CAC TCT GCC TCC AAA GGC CTA CCT CTG AAC CAT GCT GCC TTG CCT CCT       903
His Ser Ala Ser Lys Gly Leu Pro Leu Asn His Ala Ala Leu Pro Pro
540                 545                 550                 555

ACA GAC TAT GAC AGA AGT CCC TTT GTA ACA TCC CCC ATT AGC ATG ACA       951
Thr Asp Tyr Asp Arg Ser Pro Phe Val Thr Ser Pro Ile Ser Met Thr
                560                 565                 570

ATG CCC CCT CAC GGC AGC CTG CAA GGT TAC CAA ACA TAT GGC CAC TTT       999
```

```
                Met Pro Pro His Gly Ser Leu Gln Gly Tyr Gln Thr Tyr Gly His Phe
                            575                 580                 585

CCT AGC CGG GCC ATC AAG TCT GAG TAC CCA GAC CCC TAT ACC AGC TCA              1047
Pro Ser Arg Ala Ile Lys Ser Glu Tyr Pro Asp Pro Tyr Thr Ser Ser
            590                 595                 600

CCC GAG TCC ATA ATG GGC TAT TCA TAT ATG GAT AGT TAC CAG ACG AGC              1095
Pro Glu Ser Ile Met Gly Tyr Ser Tyr Met Asp Ser Tyr Gln Thr Ser
605                 610                 615

TCT CCA GCA AGC ATC CCA CAT CTG ATA CTG GAA CTT TTG AAG TGT GAG              1143
Ser Pro Ala Ser Ile Pro His Leu Ile Leu Glu Leu Leu Lys Cys Glu
620                 625                 630                 635

CCA GAT GAG CCT CAA GTC CAG GCT AAA ATC ATG GCC TAT TTG CAG CAA              1191
Pro Asp Glu Pro Gln Val Gln Ala Lys Ile Met Ala Tyr Leu Gln Gln
            640                 645                 650

GAG CAG GCT AAC CGA AGC AAG CAC GAA AAG CTG AGC ACC TTT GGG CTT              1239
Glu Gln Ala Asn Arg Ser Lys His Glu Lys Leu Ser Thr Phe Gly Leu
            655                 660                 665

ATG TGC AAA ATG GCA GAT CAA ACT CTC TTC TCC ATT GTC GAG TGG GCC              1287
Met Cys Lys Met Ala Asp Gln Thr Leu Phe Ser Ile Val Glu Trp Ala
            670                 675                 680

AGG AGT AGT ATC TTC TTC AGA GAA CTT AAG GTT GAT GAC CAA ATG AAG              1335
Arg Ser Ser Ile Phe Phe Arg Glu Leu Lys Val Asp Asp Gln Met Lys
            685                 690                 695

CTG CTT CAG AAC TGC TGG AGT GAG CTC TTA ATC CTC GAC CAC ATT TAC              1383
Leu Leu Gln Asn Cys Trp Ser Glu Leu Leu Ile Leu Asp His Ile Tyr
700                 705                 710                 715

CGA CAA GTG GTA CAT GGA AAG GAA GGA TCC ATC TTC CTG GTT ACT GGG              1431
Arg Gln Val Val His Gly Lys Glu Gly Ser Ile Phe Leu Val Thr Gly
                720                 725                 730

CAA CAA GTG GAC TAT TCC ATA ATA GCA TCA CAA GCC GGA GCC ACC CTC              1479
Gln Gln Val Asp Tyr Ser Ile Ile Ala Ser Gln Ala Gly Ala Thr Leu
                735                 740                 745

AAC AAC CTC ATG AGT CAT GCA CAG GAG TTA GTG GCA AAA CTT CGT TCT              1527
Asn Asn Leu Met Ser His Ala Gln Glu Leu Val Ala Lys Leu Arg Ser
            750                 755                 760

CTC CAG TTT GAT CAA CGA GAG TTC GTA TGT CTG AAA TTC TTG GTG CTC              1575
Leu Gln Phe Asp Gln Arg Glu Phe Val Cys Leu Lys Phe Leu Val Leu
            765                 770                 775

TTT AGT TTA GAT GTC AAA AAC CTT GAA AAC TTC CAG CTG GTA GAA GGT              1623
Phe Ser Leu Asp Val Lys Asn Leu Glu Asn Phe Gln Leu Val Glu Gly
780                 785                 790                 795

GTC CAG GAA CAA GTC AAT GCC GCC CTG CTG GAC TAC ACA ATG TGT AAC              1671
Val Gln Glu Gln Val Asn Ala Ala Leu Leu Asp Tyr Thr Met Cys Asn
                800                 805                 810

TAC CCG CAG CAG ACA GAG AAA TTT GGA CAG CTA CTT CTT CGA CTA CCC              1719
Tyr Pro Gln Gln Thr Glu Lys Phe Gly Gln Leu Leu Leu Arg Leu Pro
            815                 820                 825

GAA ATC CGG GCC ATC AGT ATG CAG GCT GAA GAA TAC CTC TAC TAC AAG              1767
Glu Ile Arg Ala Ile Ser Met Gln Ala Glu Glu Tyr Leu Tyr Tyr Lys
            830                 835                 840

CAC CTG AAC GGG GAT GTG CCC TAT AAT AAC CTT CTC ATT GAA ATG TTG              1815
His Leu Asn Gly Asp Val Pro Tyr Asn Asn Leu Leu Ile Glu Met Leu
            845                 850                 855

CAT GCC AAA AGA GCA TAAGTTACAA CCCCTAGGAG CTCTGCTTTC AAAACAAAAA              1870
His Ala Lys Arg Ala
860

GAGATTGGGG GAGTGGGGAG GGGGAAGAAG AACAGGAAGA AAAAAAGTAC TCTGAACTGC              1930

TCCAAGCAAC GCTAATTAAA AACTTGCTTT AAAGATATTG AATTTAAAAA GGCATAATAA             1990
```

```
TCAAATACTT AATAGCAAAT AAATGATGTA TCAGGGTATT TGTATTGCAA ACTGTGAATC    2050

AAAGGCTTCA CAGCCCCAGA GGATTCCATA TAAAAGACAT TGTAATGGAG TGGATTGAAC    2110

TCACAGATGG ATACCAACAC GGTCAGAAGA AAAACGGACA GAACGGTTCT TGTATATTTA    2170

AACTGATCTC CACTATGAAG AAATTTAGGA ACTAATCTTA TTAATTAGGC TTATACAGCG    2230

GGGGATTTGA GCTTACAGGA TTCCTCCATG GTAAAGCTGA ACTGAAACAA TTCTCAAGAA    2290

TGCATCAGCT GTACCTACAA TAGCCCCTCC CTCTTCCTTT GAAGGCCCGA GCACCTCTGC    2350

CCTGTGGTCA CCGAATCTGT ACTAAGGACC TGTGTTCAGC CACACCCAGT GGTAGCTCCA    2410

CCAAATCATG AACAGCCTAA TTTTGAGTGT CTGTGTCTTA GACCTGCAAA CAGCTAATAG    2470

GAAATTCTAT AATATGTTA GCTTGCCATT TTAAATATGT TCTGAGGGTT GTTTTGTCTC     2530

GTGTTCATGA TGTTAAGAAA ATGCAGGCAG TATCCCTCAT CTTATGTAAG TGTGAATTAA    2590

TATTAAGGGA AATGACTACA AACTTTCAAA GCAAATGCTC CATAGCTAAA GCAACTTAGA    2650

CCTTATTTCT GCTACTGTTG CTGAAATGTG GCTTTGGCAT TGTTGGATTT CATAAAAAAT    2710

TTCTGGCAGG AAGTCTTGTT AGTATACATC AGTCTTTTTC ATCATCCAAG TTTGTAGTTC    2770

ATTTAAAAAT ACAACATTAA ACACATTTTG CTAGGATGTC AAATAGTCAC AGTTCTAAGT    2830

AGTTGGAAAC AAAATTGACG CATGTTAATC TATGCAAAGA GAAAGGAAAG GATGAGGTGA    2890

TGTATTGACT CAAGGTTCAT TCTTGCTGCA ATTGAACATC CTCAAGAGTT GGGATGGAAA    2950

TGGTGATTTT TACATGTGTC CTGGAAAGAT ATTAAAGTAA TTCAAATCTT CCCCAAAGGG    3010

GAAAGGAAGA GAGTGATACT GACCTTTTTA AGTCATAGAC CAAAGTCTGC TGTAGAACAA    3070

ATATGGGAGG ACAAAGAATC GCAAATTCTT CAAATGACTA TTATCAGTAT TATTAACATG    3130

CGATGCCACA GGTATGAAAG TCTTGCCTTA TTTCACAATT TTAAAAGGTA GCTGTGCAGA    3190

TGTGGATCAA CATTTGTTTA AAATAAAGTA TTAATACTTT AAAGTCAAAA AAAAAAAAA    3250

A                                                                   3251

(2) INFORMATION FOR SEQ ID NO:6:

(i) SEQUENCE CHARACTERISTICS:
        (A) LENGTH: 541 amino acids
        (B) TYPE: amino acid
        (D) TOPOLOGY: linear (ii) MOLECULE TYPE: protein (xi) SEQUENCE DESCRIPTION: SEQ ID NO:6:

Met Ser Ser Asn Ser Asp Thr Gly Asp Leu Gln Glu Ser Leu Lys His
 1               5                  10                  15

Gly Leu Thr Pro Ile Gly Ala Gly Leu Pro Asp Arg His Gly Ser Pro
                20                  25                  30

Ile Pro Ala Arg Gly Arg Leu Val Met Leu Pro Lys Val Glu Thr Glu
            35                  40                  45

Ala Leu Gly Leu Ala Arg Ser His Gly Glu Gln Gly Gln Met Pro Glu
        50                  55                  60

Asn Met Gln Val Ser Gln Phe Lys Met Val Asn Tyr Ser Tyr Asp Glu
65                  70                  75                  80

Asp Leu Glu Glu Leu Cys Pro Val Cys Gly Asp Lys Val Ser Gly Tyr
                85                  90                  95

His Tyr Gly Leu Leu Thr Cys Glu Ser Cys Lys Gly Phe Phe Lys Arg
                100                 105                 110

Thr Val Gln Asn Asn Lys Arg Tyr Thr Cys Ile Glu Asn Gln Asn Cys
            115                 120                 125
```

-continued

```
Gln Ile Asp Lys Thr Gln Arg Lys Arg Cys Pro Tyr Cys Arg Phe Gln
    130                 135                 140
Lys Cys Leu Ser Val Gly Met Lys Leu Glu Ala Val Arg Ala Asp Arg
145                 150                 155                 160
Met Arg Gly Gly Arg Asn Lys Phe Gly Pro Met Tyr Lys Arg Asp Arg
                165                 170                 175
Ala Leu Lys Gln Gln Lys Lys Ala Leu Ile Arg Ala Asn Gly Leu Lys
            180                 185                 190
Leu Glu Ala Met Ser Gln Val Ile Gln Ala Met Pro Ser Asp Leu Thr
        195                 200                 205
Ile Ser Ser Ala Ile Gln Asn Ile His Ser Ala Ser Lys Gly Leu Pro
    210                 215                 220
Leu Asn His Ala Ala Leu Pro Pro Thr Asp Tyr Asp Arg Ser Pro Phe
225                 230                 235                 240
Val Thr Ser Pro Ile Ser Met Thr Met Pro Pro His Gly Ser Leu Gln
                245                 250                 255
Gly Tyr Gln Thr Tyr Gly His Phe Pro Ser Arg Ala Ile Lys Ser Glu
            260                 265                 270
Tyr Pro Asp Pro Tyr Thr Ser Ser Pro Glu Ser Ile Met Gly Tyr Ser
        275                 280                 285
Tyr Met Asp Ser Tyr Gln Thr Ser Ser Pro Ala Ser Ile Pro His Leu
    290                 295                 300
Ile Leu Glu Leu Leu Lys Cys Glu Pro Asp Glu Pro Gln Val Gln Ala
305                 310                 315                 320
Lys Ile Met Ala Tyr Leu Gln Gln Glu Gln Ala Asn Arg Ser Lys His
                325                 330                 335
Glu Lys Leu Ser Thr Phe Gly Leu Met Cys Lys Met Ala Asp Gln Thr
            340                 345                 350
Leu Phe Ser Ile Val Glu Trp Ala Arg Ser Ser Ile Phe Phe Arg Glu
        355                 360                 365
Leu Lys Val Asp Asp Gln Met Lys Leu Leu Gln Asn Cys Trp Ser Glu
    370                 375                 380
Leu Leu Ile Leu Asp His Ile Tyr Arg Gln Val Val His Gly Lys Glu
385                 390                 395                 400
Gly Ser Ile Phe Leu Val Thr Gly Gln Gln Val Asp Tyr Ser Ile Ile
                405                 410                 415
Ala Ser Gln Ala Gly Ala Thr Leu Asn Asn Leu Met Ser His Ala Gln
            420                 425                 430
Glu Leu Val Ala Lys Leu Arg Ser Leu Gln Phe Asp Gln Arg Glu Phe
        435                 440                 445
Val Cys Leu Lys Phe Leu Val Leu Phe Ser Leu Asp Val Lys Asn Leu
    450                 455                 460
Glu Asn Phe Gln Leu Val Glu Gly Val Gln Glu Gln Val Asn Ala Ala
465                 470                 475                 480
Leu Leu Asp Tyr Thr Met Cys Asn Tyr Pro Gln Gln Thr Glu Lys Phe
                485                 490                 495
Gly Gln Leu Leu Leu Arg Leu Pro Glu Ile Arg Ala Ile Ser Met Gln
            500                 505                 510
Ala Glu Glu Tyr Leu Tyr Tyr Lys His Leu Asn Gly Asp Val Pro Tyr
        515                 520                 525
Asn Asn Leu Leu Ile Glu Met Leu His Ala Lys Arg Ala
    530                 535                 540
```

-continued (2) INFORMATION FOR SEQ ID NO:7:

(i) SEQUENCE CHARACTERISTICS:
        (A) LENGTH: 2330 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 363..1862

(xi) SEQUENCE DESCRIPTION: SEQ ID NO:7:

```
GAAACTGGAT ACATGGTTTA CAGCAGGTCA CTAATGTTGG AAAAAGTACA GAGTCCAGGG      60

AAAGACTTGC TTGTAACTTT ATGAATTCTG GATTTTTTTT CCTTTGCTTT TTCTTAACTT     120

TCACTAAGGG TTACTGTAGT CTGATGTGTC CTTCCCAAGG CCACGAAATT TGACAAGCTG     180

CACTTTTCTT TTGCTCAATG ATTTCTGCTT TAAGCCAAAG AACTGCCTAT AATTTCACTA     240

AGAATGTCTT CTAATTCAGA TACTGGGGAT TTACAAGAGT CTTTAAAGCA CGGACTTACA     300

CCTATTGGTG CTGGGCTTCC GGACCGACAC GGATCCCCCA TCCCGCCCGC GGTCGCCTTG     360

TC ATG CTG CCC AAA GTG GAG ACG GAA GCC CTG GGA CTG GCT CGA TCG        407
   Met Leu Pro Lys Val Glu Thr Glu Ala Leu Gly Leu Ala Arg Ser
       545                 550                 555

CAT GGG GAA CAG GGC CAG ATG CCG GAA AAC ATG CAA GTG TCT CAA TTT       455
His Gly Glu Gln Gly Gln Met Pro Glu Asn Met Gln Val Ser Gln Phe
            560                 565                 570

AAA ATG GTG AAT TAC TCC TAT GAT GAA GAT CTG GAA GAG CTT TGT CCC       503
Lys Met Val Asn Tyr Ser Tyr Asp Glu Asp Leu Glu Glu Leu Cys Pro
        575                 580                 585

GTG TGT GGA GAT AAA GTG TCT GGG TAC CAT TAT GGG CTC CTC ACC TGT       551
Val Cys Gly Asp Lys Val Ser Gly Tyr His Tyr Gly Leu Leu Thr Cys
    590                 595                 600

GAA AGC TGC AAG GGA TTT TTT AAG CGA ACA GTC CAA AAT AAT AAA AGG       599
Glu Ser Cys Lys Gly Phe Phe Lys Arg Thr Val Gln Asn Asn Lys Arg
605                 610                 615                 620

TAC ACA TGT ATA GAA AAC CAG AAC TGC CAA ATT GAC AAA ACA CAG AGA       647
Tyr Thr Cys Ile Glu Asn Gln Asn Cys Gln Ile Asp Lys Thr Gln Arg
                625                 630                 635

AAG CGT TGT CCT TAC TGT CGT TTT CAA AAA TGT CTA AGT GTT GGA ATG       695
Lys Arg Cys Pro Tyr Cys Arg Phe Gln Lys Cys Leu Ser Val Gly Met
            640                 645                 650

AAG CTA GAA GCT GTA AGG GCC GAC CGA ATG CGT GGA GGA AGG AAT AAG       743
Lys Leu Glu Ala Val Arg Ala Asp Arg Met Arg Gly Gly Arg Asn Lys
        655                 660                 665

TTT GGG CCA ATG TAC AAG AGA GAC AGG GCC CTG AAG CAA CAG AAA AAA       791
Phe Gly Pro Met Tyr Lys Arg Asp Arg Ala Leu Lys Gln Gln Lys Lys
    670                 675                 680

GCC CTC ATC CGA GCC AAT GGA CTT AAG CTA GAA GCC ATG TCT CAG GTG       839
Ala Leu Ile Arg Ala Asn Gly Leu Lys Leu Glu Ala Met Ser Gln Val
685                 690                 695                 700

ATC CAA GCT ATG CCC TCT GAC CTG ACC ATT TCC TCT GCA ATT CAA AAC       887
Ile Gln Ala Met Pro Ser Asp Leu Thr Ile Ser Ser Ala Ile Gln Asn
                705                 710                 715

ATC CAC TCT GCC TCC AAA GGC CTA CCT CTG AAC CAT GCT GCC TTG CCT       935
Ile His Ser Ala Ser Lys Gly Leu Pro Leu Asn His Ala Ala Leu Pro
            720                 725                 730

CCT ACA GAC TAT GAC AGA AGT CCC TTT GTA ACA TCC CCC ATT AGC ATG       983
Pro Thr Asp Tyr Asp Arg Ser Pro Phe Val Thr Ser Pro Ile Ser Met
```

-continued

```
            735                 740                 745
ACA ATG CTG CAC GGC AGC CTG CAA GGT TAC CAA ACA TAT GGC CAC TTT    1031
Thr Met Leu His Gly Ser Leu Gln Gly Tyr Gln Thr Tyr Gly His Phe
    750                 755                 760

CCT AGC CGG GCC ATC AAG TCT GAG TAC CCA GAC CCC TAT ACC AGC TCA    1079
Pro Ser Arg Ala Ile Lys Ser Glu Tyr Pro Asp Pro Tyr Thr Ser Ser
765                 770                 775                 780

CCC GAG TCC ATA ATG GGC TAT TCA TAT ATG GAT AGT TAC CAG ACG AGC    1127
Pro Glu Ser Ile Met Gly Tyr Ser Tyr Met Asp Ser Tyr Gln Thr Ser
                785                 790                 795

TCT CCA GCA AGC ATC CCA CAT CTG ATA CTG GAA CTT TTG AAG TGT GAG    1175
Ser Pro Ala Ser Ile Pro His Leu Ile Leu Glu Leu Leu Lys Cys Glu
            800                 805                 810

CCA GAT GAG CCT CAA GTC CAG GCT AAA ATC ATG GCC TAT TTG CAG CAA    1223
Pro Asp Glu Pro Gln Val Gln Ala Lys Ile Met Ala Tyr Leu Gln Gln
        815                 820                 825

GAG CAG GCT AAC CGA AGC AAG CAC GAA AAG CTG AGC ACC TTT GGG CTT    1271
Glu Gln Ala Asn Arg Ser Lys His Glu Lys Leu Ser Thr Phe Gly Leu
    830                 835                 840

ATG TGC AAA ATG GCA GAT CAA ACT GTC TTC TCC ATT GTC GAG TGG GCC    1319
Met Cys Lys Met Ala Asp Gln Thr Val Phe Ser Ile Val Glu Trp Ala
845                 850                 855                 860

AGG AGT AGT ATC TTC TTC AGA GAA CTT AAG GTT GAT GAC CAA ATG AAG    1367
Arg Ser Ser Ile Phe Phe Arg Glu Leu Lys Val Asp Asp Gln Met Lys
                865                 870                 875

CTG CTT CAG AAC TGC TGG AGT GAG CTC TTA ATC CTC GAC CAC ATT TAC    1415
Leu Leu Gln Asn Cys Trp Ser Glu Leu Leu Ile Leu Asp His Ile Tyr
            880                 885                 890

CGA CAA GTG GTA CAT GGA AAG GAA GGA TCC ATC TTC CTG GTT ACT GGG    1463
Arg Gln Val Val His Gly Lys Glu Gly Ser Ile Phe Leu Val Thr Gly
        895                 900                 905

CAA CAA GTG GAC TAT TCC ATA ATA GCA TCA CAA GCC GGA GCC ACC CTC    1511
Gln Gln Val Asp Tyr Ser Ile Ile Ala Ser Gln Ala Gly Ala Thr Leu
    910                 915                 920

AAC AAC CTC ATG AGT CAT GCA CAG GAG TTA GTG GCA AAA CTT CGT TCT    1559
Asn Asn Leu Met Ser His Ala Gln Glu Leu Val Ala Lys Leu Arg Ser
925                 930                 935                 940

CTC CAG TTT GAT CAA CGA GAG TTC GTA TGT CTG AAA TTC TTG GTG CTC    1607
Leu Gln Phe Asp Gln Arg Glu Phe Val Cys Leu Lys Phe Leu Val Leu
                945                 950                 955

TTT AGT TTA GAT GTC AAA AAC CTT GAA AAC TTC CAG CTG GTA GAA GGT    1655
Phe Ser Leu Asp Val Lys Asn Leu Glu Asn Phe Gln Leu Val Glu Gly
            960                 965                 970

GTC CAG GAA CAA GTC AAT GCC GCC CTG CTG GAC TAC ACA ATG TGT AAC    1703
Val Gln Glu Gln Val Asn Ala Ala Leu Leu Asp Tyr Thr Met Cys Asn
        975                 980                 985

TAC CCG CAG CAG ACA GAG AAA TTT GGA CAG CTA CTT CTT CGA CTA CCC    1751
Tyr Pro Gln Gln Thr Glu Lys Phe Gly Gln Leu Leu Leu Arg Leu Pro
    990                 995                 1000

GAA ATC CGG GCC ATC AGT ATG CAG GCT GAA GAA TAC CTC TAC TAC AAG    1799
Glu Ile Arg Ala Ile Ser Met Gln Ala Glu Glu Tyr Leu Tyr Tyr Lys
1005                1010                1015                1020

CAC CTG AAT GGG GAT GTG CCC TAT AAT AAC CTT CTC ATT GAA ATG TTG    1847
His Leu Asn Gly Asp Val Pro Tyr Asn Asn Leu Leu Ile Glu Met Leu
                1025                1030                1035

CAT GCC AAA AGA GCA TAAGTTACAA CCCCTAGGAG CTCTGCTTTC AAAACAAAAA    1902
His Ala Lys Arg Ala
            1040

GAGATTGGGG GAGTGGGGAG GGGGAAGAAG AACAGGAAGA AAAAAAGTAC TCTGAACTGC    1962
```

```
TCCAAGTAAC GCTAATTAAA AACTTGCTTT AAAGATATTG AATTTAAAAA GGCATAATAA    2022

TCAAATACTA ATAGCAAATA AATGATGTAT CAGGGTATTT GTATTGCAAA CTGTGAATCA    2082

AAGCTTCACA GCCCCAGAGG ATTCCATATA AAAGACATTG TAATGGAGTG GATTGAACTC    2142

ACAGATGGAT ACCAACACGG TCAGAAGAAA ACGGACAGA  ACGGTTCTTG TATATTTAAA    2202

CTGATCTCCA CTATGAAGAA ATTTAGGAAC TAATCTTATT AATTAGGCTT ATACAGCGGG    2262

GATTTGAGCT TACAGGATTC CTCCATGGTA AAGCTGAACT GAAACAATTC TCAAGAATGC    2322

ATCAGCTG                                                             2330
```

(2) INFORMATION FOR SEQ ID NO:8:

(i) SEQUENCE CHARACTERISTICS:
        (A) LENGTH: 500 amino acids
        (B) TYPE: amino acid
        (D) TOPOLOGY: linear (ii) MOLECULE TYPE: protein (xi) SEQUENCE DESCRIPTION: SEQ ID NO:8:

```
Met Leu Pro Lys Val Glu Thr Glu Ala Leu Gly Leu Ala Arg Ser His
 1               5                  10                  15

Gly Glu Gln Gly Gln Met Pro Glu Asn Met Gln Val Ser Gln Phe Lys
            20                  25                  30

Met Val Asn Tyr Ser Tyr Asp Glu Asp Leu Glu Glu Leu Cys Pro Val
        35                  40                  45

Cys Gly Asp Lys Val Ser Gly Tyr His Tyr Gly Leu Leu Thr Cys Glu
    50                  55                  60

Ser Cys Lys Gly Phe Phe Lys Arg Thr Val Gln Asn Asn Lys Arg Tyr
65                  70                  75                  80

Thr Cys Ile Glu Asn Gln Asn Cys Gln Ile Asp Lys Thr Gln Arg Lys
                85                  90                  95

Arg Cys Pro Tyr Cys Arg Phe Gln Lys Cys Leu Ser Val Gly Met Lys
            100                 105                 110

Leu Glu Ala Val Arg Ala Asp Arg Met Arg Gly Gly Arg Asn Lys Phe
        115                 120                 125

Gly Pro Met Tyr Lys Arg Asp Arg Ala Leu Lys Gln Gln Lys Lys Ala
    130                 135                 140

Leu Ile Arg Ala Asn Gly Leu Lys Leu Glu Ala Met Ser Gln Val Ile
145                 150                 155                 160

Gln Ala Met Pro Ser Asp Leu Thr Ile Ser Ser Ala Ile Gln Asn Ile
                165                 170                 175

His Ser Ala Ser Lys Gly Leu Pro Leu Asn His Ala Ala Leu Pro Pro
            180                 185                 190

Thr Asp Tyr Asp Arg Ser Pro Phe Val Thr Ser Pro Ile Ser Met Thr
        195                 200                 205

Met Leu His Gly Ser Leu Gln Gly Tyr Gln Thr Tyr Gly His Phe Pro
    210                 215                 220

Ser Arg Ala Ile Lys Ser Glu Tyr Pro Asp Pro Tyr Thr Ser Ser Pro
225                 230                 235                 240

Glu Ser Ile Met Gly Tyr Ser Tyr Met Asp Ser Tyr Gln Thr Ser Ser
                245                 250                 255

Pro Ala Ser Ile Pro His Leu Ile Leu Glu Leu Leu Lys Cys Glu Pro
            260                 265                 270

Asp Glu Pro Gln Val Gln Ala Lys Ile Met Ala Tyr Leu Gln Gln Glu
```

-continued

```
               275                 280                 285
Gln Ala Asn Arg Ser Lys His Glu Lys Leu Ser Thr Phe Gly Leu Met
            290                 295                 300
Cys Lys Met Ala Asp Gln Thr Val Phe Ser Ile Val Glu Trp Ala Arg
305                 310                 315                 320
Ser Ser Ile Phe Phe Arg Glu Leu Lys Val Asp Asp Gln Met Lys Leu
                325                 330                 335
Leu Gln Asn Cys Trp Ser Glu Leu Leu Ile Leu Asp His Ile Tyr Arg
            340                 345                 350
Gln Val Val His Gly Lys Glu Gly Ser Ile Phe Leu Val Thr Gly Gln
            355                 360                 365
Gln Val Asp Tyr Ser Ile Ile Ala Ser Gln Ala Gly Ala Thr Leu Asn
        370                 375                 380
Asn Leu Met Ser His Ala Gln Glu Leu Val Ala Lys Leu Arg Ser Leu
385                 390                 395                 400
Gln Phe Asp Gln Arg Glu Phe Val Cys Leu Lys Phe Leu Val Leu Phe
                405                 410                 415
Ser Leu Asp Val Lys Asn Leu Glu Asn Phe Gln Leu Val Glu Gly Val
            420                 425                 430
Gln Glu Gln Val Asn Ala Ala Leu Leu Asp Tyr Thr Met Cys Asn Tyr
        435                 440                 445
Pro Gln Gln Thr Glu Lys Phe Gly Gln Leu Leu Leu Arg Leu Pro Glu
    450                 455                 460
Ile Arg Ala Ile Ser Met Gln Ala Glu Glu Tyr Leu Tyr Tyr Lys His
465                 470                 475                 480
Leu Asn Gly Asp Val Pro Tyr Asn Asn Leu Leu Ile Glu Met Leu His
                485                 490                 495
Ala Lys Arg Ala
        500
```

(2) INFORMATION FOR SEQ ID NO:9:

(i) SEQUENCE CHARACTERISTICS:
        (A) LENGTH: 3027 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 159..1838

(xi) SEQUENCE DESCRIPTION: SEQ ID NO:9:

```
TGTTTTTTCC CCCTTTTTCT TAACTTTCAC TAAGGAAATG AGGGTTACTG TAGTCTGAGG        60

TTTCCTTCCC AAAGTCACAA AATATGACAA GCTGCAATCT TTCTCACATT CAATGATTTC       120

TGCTGTAAGC CAAAGGACTG CCAATAATTT CGCTAAGA ATG TCT GCT AGT TTG          173
                                         Met Ser Ala Ser Leu
                                                         505

GAT ACT GGA GAT TTT CAA GAA TTT CTT AAG CAT GGA CTT ACA GCT ATT       221
Asp Thr Gly Asp Phe Gln Glu Phe Leu Lys His Gly Leu Thr Ala Ile
                510                 515                 520

GCG TCT GCA CCA GGG TCA GAG ACT CGC CAC TCC CCC AAA CGT GAG GAA       269
Ala Ser Ala Pro Gly Ser Glu Thr Arg His Ser Pro Lys Arg Glu Glu
            525                 530                 535

CAA CTC CGG GAA AAA CGT GCT GGG CTT CCG GAC CGA CAC CGA CGC CCC       317
Gln Leu Arg Glu Lys Arg Ala Gly Leu Pro Asp Arg His Arg Arg Pro
```

```
                540                 545                     550
ATT CCC GCC CGC AGC CGC CTT GTC ATG CTG CCC AAA GTG GAG ACG GAA       365
Ile Pro Ala Arg Ser Arg Leu Val Met Leu Pro Lys Val Glu Thr Glu
    555                 560                 565

GCC CCA GGA CTG GTC CGA TCG CAT GGG GAA CAG GGG CAG ATG CCA GAA       413
Ala Pro Gly Leu Val Arg Ser His Gly Glu Gln Gly Gln Met Pro Glu
570                 575                 580                 585

AAC ATG CAA GTG TCT CAA TTT AAA ATG GTG AAT TAC TCC TAT GAT GAA       461
Asn Met Gln Val Ser Gln Phe Lys Met Val Asn Tyr Ser Tyr Asp Glu
                590                 595                 600

GAT CTG GAA GAG CTA TGT CCT GTG TGT GGC GAT AAA GTG TCT GGG TAC       509
Asp Leu Glu Glu Leu Cys Pro Val Cys Gly Asp Lys Val Ser Gly Tyr
            605                 610                 615

CAT TAC GGT CTC CTC ACG TGC GAA AGC TGC AAG GGT TTT TTT AAG CGA       557
His Tyr Gly Leu Leu Thr Cys Glu Ser Cys Lys Gly Phe Phe Lys Arg
        620                 625                 630

ACT GTC CAA AAC CAA AAA AGG TAC ACG TGC ATA GAG AAC CAG AAT TGC       605
Thr Val Gln Asn Gln Lys Arg Tyr Thr Cys Ile Glu Asn Gln Asn Cys
    635                 640                 645

CAA ATT GAC AAA ACG CAG AGA AAA CGA TGT CCC TAC TGT CGA TTC AAA       653
Gln Ile Asp Lys Thr Gln Arg Lys Arg Cys Pro Tyr Cys Arg Phe Lys
650                 655                 660                 665

AAA TGT ATC GAT GTT GGG ATG AAG CTG GAA GCC GTA AGA GCC GAC CGC       701
Lys Cys Ile Asp Val Gly Met Lys Leu Glu Ala Val Arg Ala Asp Arg
                670                 675                 680

ATG CGA GGG GGC AGA AAT AAG TTT GGG CCA ATG TAC AAG AGA GAC AGG       749
Met Arg Gly Gly Arg Asn Lys Phe Gly Pro Met Tyr Lys Arg Asp Arg
            685                 690                 695

GCT TTG AAG CAG CAG AAG AAA GCC CTC ATT CGA GCC AAT GGA CTT AAG       797
Ala Leu Lys Gln Gln Lys Lys Ala Leu Ile Arg Ala Asn Gly Leu Lys
        700                 705                 710

CTG GAA GCC ATG TCT CAG GTG ATC CAA GCA ATG CCC TCA GAC CTG ACC       845
Leu Glu Ala Met Ser Gln Val Ile Gln Ala Met Pro Ser Asp Leu Thr
    715                 720                 725

TCT GCA ATT CAG AAC ATT CAT TCC GCC TCC AAA GGC CTA CCT CTG AGC       893
Ser Ala Ile Gln Asn Ile His Ser Ala Ser Lys Gly Leu Pro Leu Ser
730                 735                 740                 745

CAT GTA GCC TTG CCT CCG ACA GAC TAT GAC AGA AGT CCC TTT GTC ACA       941
His Val Ala Leu Pro Pro Thr Asp Tyr Asp Arg Ser Pro Phe Val Thr
                750                 755                 760

TCT CCC ATT AGC ATG ACA ATG CCA CCT CAC AGC AGC CTG CAT GGT TAC       989
Ser Pro Ile Ser Met Thr Met Pro Pro His Ser Ser Leu His Gly Tyr
            765                 770                 775

CAA CCC TAT GGT CAC TTT CCT AGT CGG GCC ATC AAG TCT GAG TAC CCA      1037
Gln Pro Tyr Gly His Phe Pro Ser Arg Ala Ile Lys Ser Glu Tyr Pro
        780                 785                 790

GAC CCC TAC TCC AGC TCA CCT GAG TCA ATG ATG GGT TAC TCC TAC ATG      1085
Asp Pro Tyr Ser Ser Ser Pro Glu Ser Met Met Gly Tyr Ser Tyr Met
    795                 800                 805

GAT GGT TAC CAG ACA AAC TCC CCG GCC AGC ATC CCA CAC CTG ATA CTG      1133
Asp Gly Tyr Gln Thr Asn Ser Pro Ala Ser Ile Pro His Leu Ile Leu
810                 815                 820                 825

GAA CTT TTG AAG TGT GAA CCA GAT GAG CCT CAA GTT CAA GCG AAG ATC      1181
Glu Leu Leu Lys Cys Glu Pro Asp Glu Pro Gln Val Gln Ala Lys Ile
                830                 835                 840

ATG GCT TAC CTC CAG CAA GAG CAG AGT AAC CGA AAC AGG CAA GAA AAG      1229
Met Ala Tyr Leu Gln Gln Glu Gln Ser Asn Arg Asn Arg Gln Glu Lys
            845                 850                 855

CTG AGC GCA TTT GGG CTT TTA TGC AAA ATG GCG GAC CAG ACC CTG TTC      1277
```

```
Leu Ser Ala Phe Gly Leu Leu Cys Lys Met Ala Asp Gln Thr Leu Phe
        860                 865                 870

TCC ATT GTT GAG TGG GCC AGG AGT AGT ATC TTC TTC AGG GAA CTG AAG       1325
Ser Ile Val Glu Trp Ala Arg Ser Ser Ile Phe Phe Arg Glu Leu Lys
875                 880                 885

GTT GAT GAC CAA ATG AAG CTG CTT CAA AAC TGC TGG AGT GAG CTC TTG       1373
Val Asp Asp Gln Met Lys Leu Leu Gln Asn Cys Trp Ser Glu Leu Leu
890                 895                 900                 905

ATT CTC GAT CAC ATT TAC CGA CAA GTG GCG CAT GGG AAG GAA GGG ACA       1421
Ile Leu Asp His Ile Tyr Arg Gln Val Ala His Gly Lys Glu Gly Thr
                910                 915                 920

ATC TTC CTG GTT ACT GGA GAA CAC GTG GAC TAC TCC ACC ATC ATC TCA       1469
Ile Phe Leu Val Thr Gly Glu His Val Asp Tyr Ser Thr Ile Ile Ser
                925                 930                 935

CAC ACA GAA GTC GCG TTC AAC AAC CTC CTG AGT CTC GCA CAG GAG CTG       1517
His Thr Glu Val Ala Phe Asn Asn Leu Leu Ser Leu Ala Gln Glu Leu
            940                 945                 950

GTG GTG AGG CTC CGT TCC CTT CAG TTC GAT CAG CGG GAG TTT GTA TGT       1565
Val Val Arg Leu Arg Ser Leu Gln Phe Asp Gln Arg Glu Phe Val Cys
            955                 960                 965

CTC AAG TTC CTG GTG CTG TTC AGC TCA GAT GTG AAG AAC CTG GAG AAC       1613
Leu Lys Phe Leu Val Leu Phe Ser Ser Asp Val Lys Asn Leu Glu Asn
970                 975                 980                 985

CTG CAG CTG GTG GAA GGT GTC CAA GAG CAG GTG AAT GCC GCC CTG CTG       1661
Leu Gln Leu Val Glu Gly Val Gln Glu Gln Val Asn Ala Ala Leu Leu
                990                 995                 1000

GAC TAC ACG GTT TGC AAC TAC CCA CAA CAG ACT GAG AAA TTC GGA CAG       1709
Asp Tyr Thr Val Cys Asn Tyr Pro Gln Gln Thr Glu Lys Phe Gly Gln
            1005                1010                1015

CTA CTT CTT CGG CTA CCC GAG ATC CGG GCA ATC AGC AAG CAG GCA GAA       1757
Leu Leu Leu Arg Leu Pro Glu Ile Arg Ala Ile Ser Lys Gln Ala Glu
        1020                1025                1030

GAC TAC CTG TAC TAT AAG CAC GTG AAC GGG GAT GTG CCC TAT AAT AAC       1805
Asp Tyr Leu Tyr Tyr Lys His Val Asn Gly Asp Val Pro Tyr Asn Asn
    1035                1040                1045

CTC CTC ATT GAG ATG CTG CAT GCC AAA AGA GCC TAAGTCCCCA CCCCTGGAAG     1858
Leu Leu Ile Glu Met Leu His Ala Lys Arg Ala
1050                1055                1060

CTTGCTCTAG GAACACAGAC TGGAAGGAGA AGAGGAGGAC GATGACAGAA ACACAATACT     1918

CTGAACTGCT CCAAGCAATG CTAATTATAA ACTTGGTTTA AAGACACTGA ATTTTAAAAG     1978

CATAATAATT AAATACCTAA TAGCAAATAA ATGATATATC AGGGTATTTG TACTGCAAAC     2038

TGTGAATCAA AGGCTGTATG AATCAAAGGA TTCATATGAA AGACATTGTA ATGGGGTGGA     2098

TTGAACTTAC AGATGGAGAC CAATACCACA GCAGAATAAA AATGGACAGA ACAATCCTTG     2158

TATATTTAAA CTAATCTGCT ATTAAGAAAT TCAGAAGTTG ATCTCTGTTA TTAATTGGAT     2218

TTGTCCTGAA TTACTCCGTG GTGACGCTGA ACAACTCAAG AATACATGGG CTGTGCTTGG     2278

CAGCCCCTCC CCATCCCTCC CACCACCACC ACCCCCACCC CCACAAGGCC CTATACCTTC     2338

TGACCTGTGA GCCCTGAAGC TATTTTAAGG ACTTCTGTTC AGCCATACCC AGTAGTAGCT     2398

CCACTAAACC ATGATTTCTG GATGTCTGTG TCTTAGACCT GCCAACAGCT AATAAGAACA     2458

ATGTATAAAT ATGTCAGCTT GCATTTTAAA TATGTGCTGA AGTTTGTTTT GTCGTGTGTT     2518

CGTAATTAAA AAGAAAACGG GCAGTAACCC TCTTCTATAT AAGCATTAGT TAATATTAAG     2578

GGAAATCAAA CAAATCTAAG CCAATACTCC CAACAAGCAA GTTAGATCTT ACTTCTGCTG     2638

CTGTTGCTGA AATGTGGCTT TGGCATGGTT GGGTTTCATA AAACTTTTTG GCCAAGAGGC     2698
```

-continued

| | |
|---|---|
| TTGTTAGTAT ACATCCATCT GTTTAGTCAT CAAGGTTTGT AGTTCACTTA AAAAAAAATA | 2758 |
| AACCACTAGA CATCTTTTGC TGAATGTCAA ATAGTCACAG TCTAAGTAGC CAAAAAGTCA | 2818 |
| AAGCGTGTTA AACATTGCCA AATGAAGGAA AGGGTGAGCT GCAAAGGGGA TGGTTCGAGG | 2878 |
| TTCATTCCAG TTGTGACCCG AGCGTCCCCA AAACCTGGGA TGCAAAGACA GTGATTCTGC | 2938 |
| ATATGGCCTG GAAAGACAGG AAAGCCAGTC TCCTACAAAG GGGAATGGAA GATCCTGGCC | 2998 |
| TCTAAGTCAT AGACCAAAGT CTGCTGTAG | 3027 |

(2) INFORMATION FOR SEQ ID NO:10:

(i) SEQUENCE CHARACTERISTICS:
        (A) LENGTH: 560 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ser Ala Ser Leu Asp Thr Gly Asp Phe Gln Glu Phe Leu Lys His
 1               5                  10                  15

Gly Leu Thr Ala Ile Ala Ser Ala Pro Gly Ser Glu Thr Arg His Ser
                20                  25                  30

Pro Lys Arg Glu Glu Gln Leu Arg Glu Lys Arg Ala Gly Leu Pro Asp
            35                  40                  45

Arg His Arg Arg Pro Ile Pro Ala Arg Ser Arg Leu Val Met Leu Pro
        50                  55                  60

Lys Val Glu Thr Glu Ala Pro Gly Leu Val Arg Ser His Gly Glu Gln
 65                  70                  75                  80

Gly Gln Met Pro Glu Asn Met Gln Val Ser Gln Phe Lys Met Val Asn
                85                  90                  95

Tyr Ser Tyr Asp Glu Asp Leu Glu Glu Leu Cys Pro Val Cys Gly Asp
            100                 105                 110

Lys Val Ser Gly Tyr His Tyr Gly Leu Leu Thr Cys Glu Ser Cys Lys
        115                 120                 125

Gly Phe Phe Lys Arg Thr Val Gln Asn Gln Lys Arg Tyr Thr Cys Ile
    130                 135                 140

Glu Asn Gln Asn Cys Gln Ile Asp Lys Thr Gln Arg Lys Arg Cys Pro
145                 150                 155                 160

Tyr Cys Arg Phe Lys Lys Cys Ile Asp Val Gly Met Lys Leu Glu Ala
                165                 170                 175

Val Arg Ala Asp Arg Met Arg Gly Gly Arg Asn Lys Phe Gly Pro Met
            180                 185                 190

Tyr Lys Arg Asp Arg Ala Leu Lys Gln Gln Lys Lys Ala Leu Ile Arg
        195                 200                 205

Ala Asn Gly Leu Lys Leu Glu Ala Met Ser Gln Val Ile Gln Ala Met
    210                 215                 220

Pro Ser Asp Leu Thr Ser Ala Ile Gln Asn Ile His Ser Ala Ser Lys
225                 230                 235                 240

Gly Leu Pro Leu Ser His Val Ala Leu Pro Pro Thr Asp Tyr Asp Arg
                245                 250                 255

Ser Pro Phe Val Thr Ser Pro Ile Ser Met Thr Met Pro Pro His Ser
            260                 265                 270

Ser Leu His Gly Tyr Gln Pro Tyr Gly His Phe Pro Ser Arg Ala Ile
        275                 280                 285

Lys Ser Glu Tyr Pro Asp Pro Tyr Ser Ser Ser Pro Glu Ser Met Met
```

```
                   290                 295                 300
Gly Tyr Ser Tyr Met Asp Gly Tyr Gln Thr Asn Ser Pro Ala Ser Ile
305                 310                 315                 320

Pro His Leu Ile Leu Glu Leu Leu Lys Cys Glu Pro Asp Glu Pro Gln
                    325                 330                 335

Val Gln Ala Lys Ile Met Ala Tyr Leu Gln Gln Glu Gln Ser Asn Arg
                340                 345                 350

Asn Arg Gln Glu Lys Leu Ser Ala Phe Gly Leu Leu Cys Lys Met Ala
            355                 360                 365

Asp Gln Thr Leu Phe Ser Ile Val Glu Trp Ala Arg Ser Ser Ile Phe
        370                 375                 380

Phe Arg Glu Leu Lys Val Asp Asp Gln Met Lys Leu Leu Gln Asn Cys
385                 390                 395                 400

Trp Ser Glu Leu Leu Ile Leu Asp His Ile Tyr Arg Gln Val Ala His
                    405                 410                 415

Gly Lys Glu Gly Thr Ile Phe Leu Val Thr Gly Glu His Val Asp Tyr
                420                 425                 430

Ser Thr Ile Ile Ser His Thr Glu Val Ala Phe Asn Asn Leu Leu Ser
            435                 440                 445

Leu Ala Gln Glu Leu Val Val Arg Leu Arg Ser Leu Gln Phe Asp Gln
        450                 455                 460

Arg Glu Phe Val Cys Leu Lys Phe Leu Val Leu Phe Ser Ser Asp Val
465                 470                 475                 480

Lys Asn Leu Glu Asn Leu Gln Leu Val Glu Gly Val Gln Glu Gln Val
                    485                 490                 495

Asn Ala Ala Leu Leu Asp Tyr Thr Val Cys Asn Tyr Pro Gln Gln Thr
                500                 505                 510

Glu Lys Phe Gly Gln Leu Leu Leu Arg Leu Pro Glu Ile Arg Ala Ile
            515                 520                 525

Ser Lys Gln Ala Glu Asp Tyr Leu Tyr Tyr Lys His Val Asn Gly Asp
        530                 535                 540

Val Pro Tyr Asn Asn Leu Leu Ile Glu Met Leu His Ala Lys Arg Ala
545                 550                 555                 560

(2) INFORMATION FOR SEQ ID NO:11:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:11:

Ile Leu Arg Lys Leu Leu Gln Glu
1               5
```